(12) United States Patent  (10) Patent No.: US 7,497,910 B2
Mey et al.  (45) Date of Patent: Mar. 3, 2009

(54) DRY POWDER ELECTROSTATIC DEPOSITION METHOD AND APPARATUS

(75) Inventors: William Mey, Rochester, NY (US); William J. Grande, Pittsford, NY (US)

(73) Assignee: Tiger Microsystems, Inc., Pittsford, NY (US)

( * ) Notice: Subject to any disclaimer, the term of this patent is extended or adjusted under 35 U.S.C. 154(b) by 0 days.

(21) Appl. No.: 10/177,209

(22) Filed: Jun. 21, 2002

(65) Prior Publication Data

US 2002/0195053 A1  Dec. 26, 2002

Related U.S. Application Data

(60) Provisional application No. 60/301,070, filed on Jun. 26, 2001.

(51) Int. Cl.
 *B05C 5/02* (2006.01)
(52) U.S. Cl. .................. 118/623; 118/625; 118/629; 118/630
(58) Field of Classification Search ........... 118/629, 118/630, 631, 632, 624, 625, 623, 621; 427/466, 427/469, 2.14
 See application file for complete search history.

(56) References Cited

U.S. PATENT DOCUMENTS 3,914,771 A  10/1975 Lunde et al.
4,307,555 A  12/1981 Mlodozeniec et al.

(Continued)

*Primary Examiner*—George R Koch, III
(74) *Attorney, Agent, or Firm*—Thomas R. FitzGerald, Esq.; Hiscock & Barclay, LLP

(57) ABSTRACT

A method and apparatus are presented for electrostatic deposition of dry powder to a tablet, capsule, or a specific area of any of a wide range of pharmaceutical substrates. The apparatus includes: a magnetic brush having a rotatable multi-pole magnetic core and a stationary outer shell; a developer supply for supplying a magnetic developer powder, consisting of a magnetic carrier particles and pharmaceutical dry powder particles, to the magnetic brush; a print head on the outer shell; a tablet or other pharmaceutical substrate arranged in spaced relation to the print head to define a pharmaceutical powder transfer region through which the substrate can be moved. The print head includes an array of microchannels for forming a plurality of parallel lines of developer in the channels, a corresponding plurality of transfer electrodes located in the microchannels for selectively transferring pharmaceutical powder from the lines to a substrate, driver circuitry for generating and applying transfer signals to the transfer electrodes, a power supply connection for applying power to the drive circuitry, a print signal input connection for applying print signals to the print head, and a logic and control circuit for applying the print signals to the drive circuitry.

In one embodiment the width of an individual microchannel print head and the rotating multipole magnetic core is approximately the same dimension as the tablet or substrate to which pharmaceutical powder is to be deposited. In a further embodiment individual microchannel print heads can be arranged along the length of the shell to simultaneously deposit pharmaceutical powder to an array of tablets. In still a further embodiment the microchannel print head is shaped to conform to the tablet or capsule geometry to enhance deposition in three dimensions.

In another embodiment the microchannel print head is formed on a silicon substrate onto which are also formed a multiplicity of individual drive circuits connected through separate conductive paths to individual transfer electrodes. In a further embodiment all the microelectronic circuitry necessary for the operation of the integrated microchannel print head is formed on the silicon substrate.

39 Claims, 18 Drawing Sheets

U.S. PATENT DOCUMENTS

| | | |
|---|---|---|
| 4,780,733 A | 10/1988 | Schmidlin |
| 5,038,159 A | 8/1991 | Schmidlin et al. |
| 5,307,092 A | 4/1994 | Larson |
| 5,402,158 A | 3/1995 | Larson |
| 5,650,809 A | 7/1997 | Kitamura |
| 5,682,586 A | 10/1997 | Stephany et al. |
| 5,701,552 A | 12/1997 | Stephany et al. |
| 5,714,007 A | 2/1998 | Pletcher et al. |
| 5,729,884 A | 3/1998 | Stephany et al. |
| 5,818,476 A | 10/1998 | Mey et al. |
| 5,821,972 A | 10/1998 | Mey et al. |
| 5,846,595 A | 12/1998 | Sun et al. |
| 5,858,099 A | 1/1999 | Sun et al. |
| 5,889,544 A | 3/1999 | Mey et al. |
| 5,912,691 A | 6/1999 | Mey et al. |
| 5,971,732 A | 10/1999 | Grisch et al. |
| 5,988,794 A | 11/1999 | Takagi |
| 6,007,630 A | 12/1999 | Pletcher et al. |
| 6,037,957 A | 3/2000 | Grande et al. |
| 6,063,194 A | 5/2000 | Poliniak et al. |
| 6,074,688 A | 6/2000 | Pletcher et al. |
| 6,095,164 A * | 8/2000 | Saitoh et al. ............... 134/113 |
| 6,117,479 A * | 9/2000 | Hogan et al. ............... 427/2.14 |
| 6,221,438 B1 | 4/2001 | Matthies |
| 6,400,385 B1 | 6/2002 | Grande et al. |
| 2002/0197388 A1* | 12/2002 | Brown et al. ............... 427/2.1 |

* cited by examiner

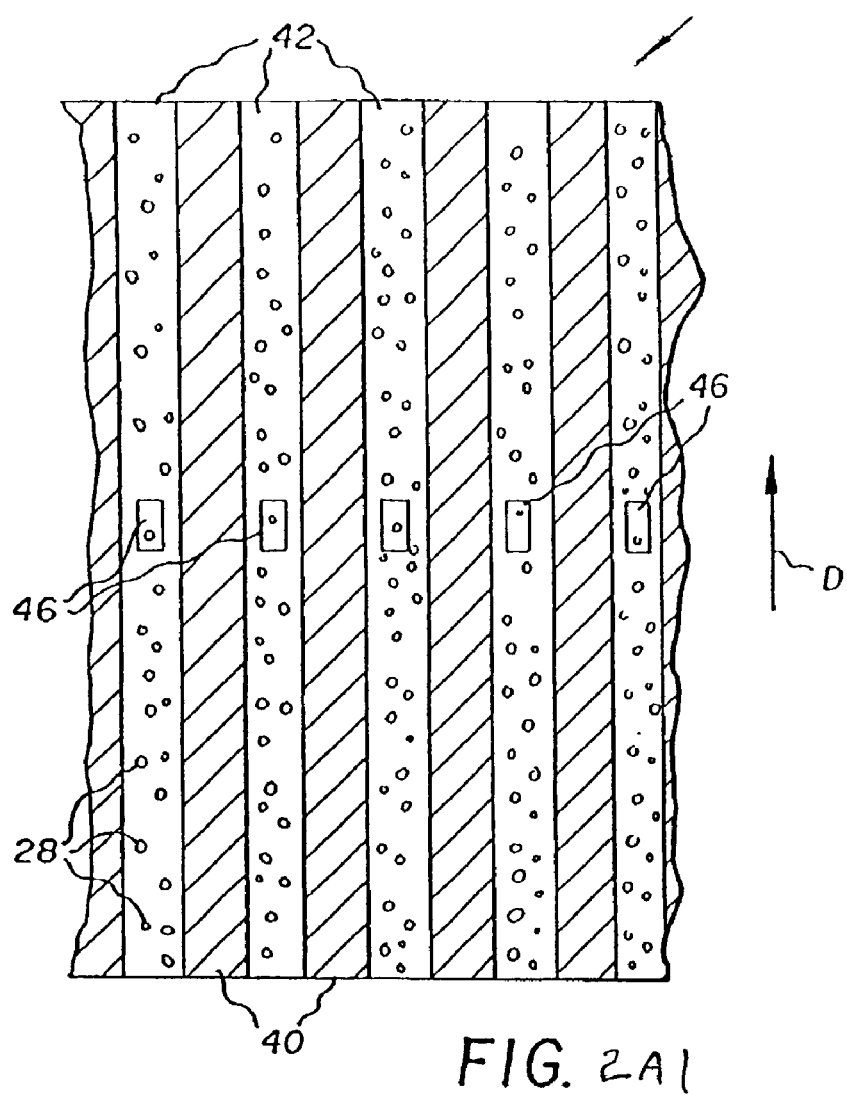
FIG. 2A1
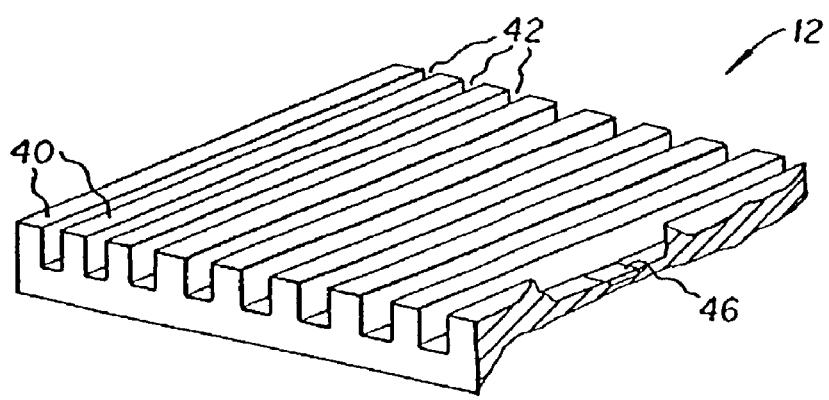
FIG. 2A2

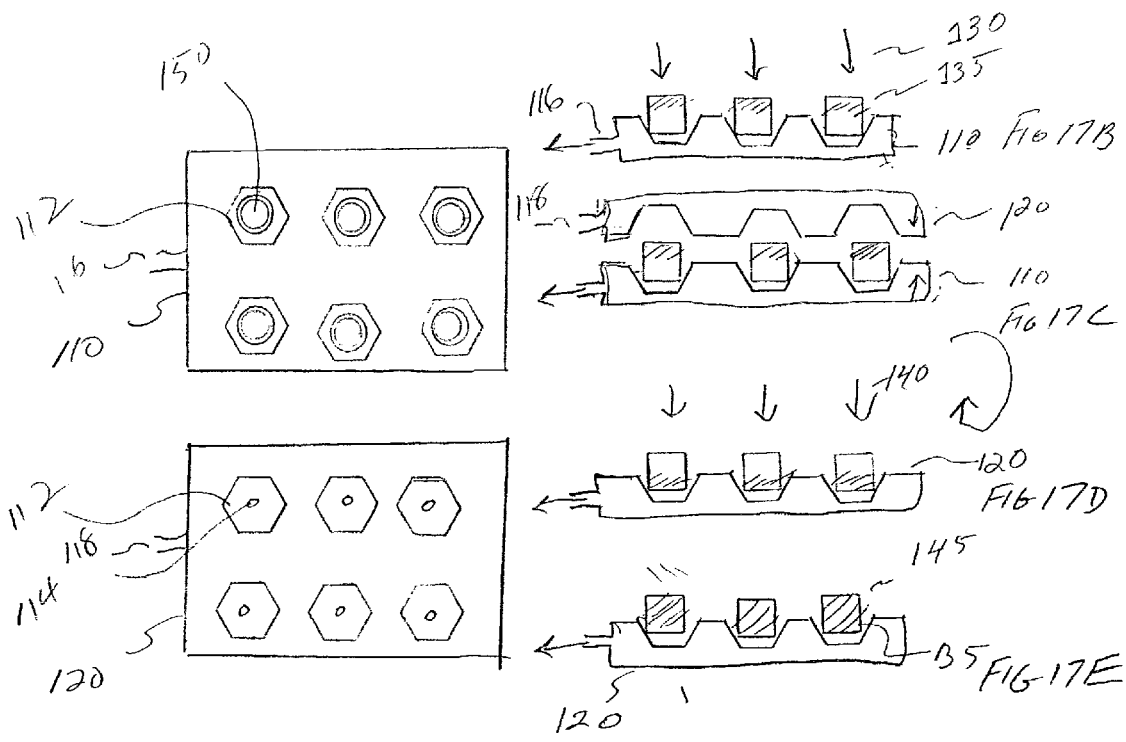
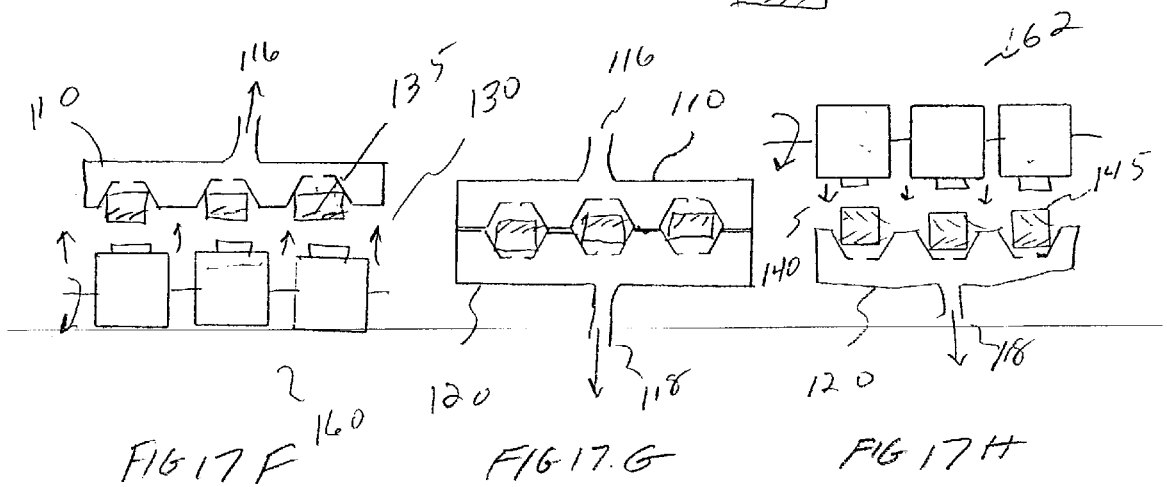
FIG 17A, FIG 17B, FIG 17C, FIG 17D, FIG 17E, FIG 17F, FIG 17G, FIG 17H

DRY POWDER ELECTROSTATIC DEPOSITION METHOD AND APPARATUS

CROSS-REFERENCE TO RELATED APPLICATIONS

This application claims the benefit of the priority date of Provisional Patent Application Ser. No. 60/301,070 filed Jun. 26, 2001.

FIELD OF INVENTION

The invention relates generally to the field of dry powder electrostatic deposition and in particular to a method and apparatus for the deposition of pharmaceutical medicament powder or drugs to a substrate.

DISCUSSION OF PRIOR ART

Powdered medication is typically administered orally to a person as a tablet or capsule, or as an inhalant. The prior art discloses a number of methods for depositing a powdered medication using electrostatics. One example is disclosed in U.S. Pat. No. 6,074,688, issued Jun. 13, 2000. This patent describes a method for electrostatically depositing doses of medicament powder at select locations on a substrate. The apparatus described contains a charged particle emitter, such as an ionographic print head, for generating charged particles. These particles charge a predefined region of a substrate such as a tablet in order to attract the powdered medication. The apparatus controls the medicament dosage by tribo-charging the powder and controls the deposition location by charging a specific region of the substrate. In order to deposit medicament dosage at a specific or predefined region of a substrate, the substrate must be charged. An ionographic print head may be used for charging the substrate.

This approach to medication deposition has disadvantages. Charging a substrate implies that the substrate is a dielectric layer positioned upon a conductive plate or conductive substrate. To practice the above art the dielectric substrate, e.g., a tablet cannot be conductive. This restricts the use of the described approach to non-conductive tablets, a first disadvantage.

The use of an ionographic print head or similar device to form the electrostatic charge creates ions which may chemically interact with the medicament. Such chemical interaction may cause the medicament to change its properties, a second disadvantage.

Furthermore, the deposition must be carried out in air or some gas to provide means to form the ions for electrostatically charging a specific region of the substrate. This restricts the above approach to methods which operate with an available ion supply in gas form, a third disadvantage.

Another example of prior art for packaging of medicament dry powders using electrostatics is described in U.S. Pat. No. 5,960,609, issued Oct. 5, 1999. This patent describes a method of first creating an electrostatic charge on a specific area of a substrate using an ionographic print head. Then an electrostatically charged dry pharmaceutical powder or drug is brought near, or in contact with, the electrostatically charged area of the substrate where it is attracted to the charged area. This dry powder is then transported by the substrate or powder carrier surface to a transfer station where the dry powder is transferred to a receiver such as an open ended capsule or other type of receiving substrate. The receiving substrate may be a tablet, open ended capsule, edible materials such as starch, as examples. This approach has the disadvantage of the added transfer steps from source to carrier surface to receiving substrate. It also has the last two disadvantages of the approach described previously.

Methods other than the use of ionographic print heads noted in the prior art above can be employed to create the latent electrostatic image. In place of an ionographic print head, more conventional electrophotographic methods can be used. As pointed out in U.S. Pat. No. 5,960,609, photons can be used to create the latent image. In this case, however, a photoconductor and corona charger must be used to create a latent image. After developing this latent image with pharmaceutical material, the material must be transferred to the desired substrate. Also, when using an ionographic print head or a corona charger with a photoconductor, the substrate that receives the ions and subsequently the pharmaceutical powder must be either a dielectric or a photodielectric material. Again, the disadvantages are similar.

The prior art described above utilizes much of the technology commonly used in electrophotography. In existing applications of this technology, the toner is not a pharmaceutical material but a pigmented material used for printing. In electrophotography, a photoconductor is corona charged and then exposed to a pattern of radiation to form an electrostatic charge pattern or latent image. The charge pattern is developed by transferring toner to the photoconductor from a developer supply station to form a toner image. The toner image is subsequently transferred to paper or another substrate where is it fused to form the final output. The photoconductor, corona charger and radiation source is sometimes replaced with an ionographic print head and this method is commonly referred to an ionography.

The use of electrostatics for the deposition of pharmaceutical materials as described above utilizes many of the subsystems and technology commonly used in electrophotography and ionography. This usage is distinguished chiefly by the use of pharmaceutical materials for the toner and tablets, capsules or other receivers for the substrate.

Another method of coating a substrate with a pharmaceutical powder is described in U.S. Pat. No. 6,117,479 issued on Sep. 12, 2000. This method describes coating electrically poor conducting substrates by bringing the substrate to a coating station at which the substrate and the coating material are held at different potentials. The potential difference is sufficient to coat the exposed surface of the substrate with the pharmaceutical powder. In this method the entire substrate is coated since there is no latent image of ions deposited on a specific area of the substrate. The inventors do state that the source of particulate coating materials may be a multiple source comprising several sub-sources of different color coating material, and hence, tablets having more than one color on a single side can be provided. How this is accomplished is unclear and the patent gives no guidance as to the method used.

To sum up, the prior art has not addressed the problem of electrostatic deposition of pharmaceutical dry powders in a specific area of a substrate without either the use of either an ionographic print head or the use of an electrophotographic method employing a corona charger, photoconductor and radiation source. Ions generated from either an ionographic print head or a corona charger are highly reactive and could alter the chemical properties of the pharmaceutical materials during deposition. Both an ionographic print head and a corona charger emit ions used for creating an electrostatic latent image. A by-product of creating ions is ozone generation, a health hazard. It would be an advantage to eliminate these devices and deposit the pharmaceutical material or drug directly onto a specific area of a substrate or receiver. It would also be an advantage to be able to deposit pharmaceutical powders or drugs on either dielectric or conductive substrates.

SUMMARY

The present invention describes a technology to be used for electrostatic deposition of dry powder to a specific area of a pharmaceutical substrate. Briefly summarized, according to one aspect of the present invention, a method and apparatus is described for the deposition of pharmaceutical medicament powder or drugs to a specific area of a tablet, capsule or other types of pharmaceutical substrates. The apparatus includes the following: a magnetic brush having a rotating multi-pole magnetic core and a stationary outer shell; a developer supply for supplying a magnetic developer powder, comprising magnetic carrier particles and pharmaceutical dry powder particles; a magnetic brush; a print head on the outer shell; a tablet or other pharmaceutical substrate arranged in spaced relation to the print head to define a pharmaceutical powder transfer region through which the substrate can be moved. The print head includes an array of microchannels for forming a plurality of parallel lines of developer in the channels, a corresponding plurality of transfer electrodes located in the microchannels for selectively transferring pharmaceutical powder from the lines to a substrate, driver circuitry for generating and applying transfer signals to the transfer electrodes, a power supply connection for applying power to the drive circuitry, a print signal input connection for applying print signals to the print head, and a logic and control circuit for applying the print signals to the drive circuitry.

In one embodiment the width of an individual microchannel print head and the rotating multipole magnetic core is approximately the same dimension as the tablet or substrate to which pharmaceutical powder is to be deposited. In a further embodiment an individual microchannel print head can be arranged along the length of the shell to simultaneously deposit pharmaceutical powder to an array of tablets. In still a further embodiment the microchannel print head is shaped to conform to the tablet or capsule geometry to enhance deposition in three dimensions.

In another embodiment the microchannel print head is formed on a silicon substrate onto which are also formed a multiplicity of individual drive circuits connected through separate conductive paths to individual transfer electrodes. In a further embodiment all the microelectronic circuitry necessary for the operation of the integrated microchannel print head is formed on the silicon substrate.

These and other aspects, objects, features, and advantages of the present invention will be more clearly understood and appreciated from a review of the following detailed description of the preferred embodiments and appended claims and by reference to the accompanying drawings.

DESCRIPTION OF DRAWINGS

FIG. 2A1 is a partial plan view of the microchannel print head employed in the invention;

FIG. 2A2 is a partial perspective view of the microchannel print head employed in the present invention;

FIGS. 17a-17h show steps in a double sided coating process.

To facilitate understanding, identical references numerals have been used, where possible, to designate identical elements that are common to the figures.

Figure 1:
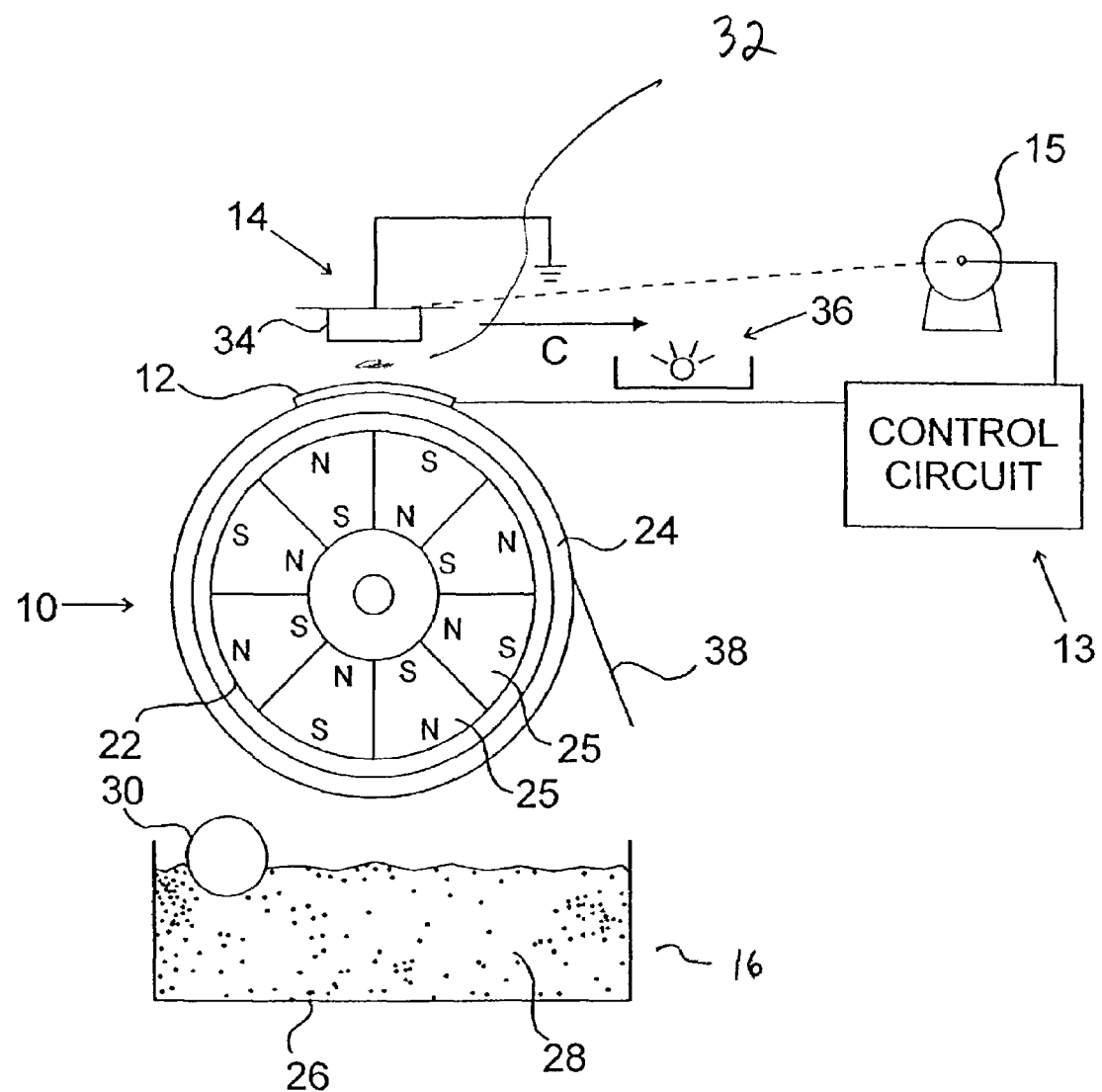
FIG. 1 is a schematic diagram of a device for depositing dry powder pharmaceuticals of drugs on a substrate employing a microchannel print head according to the present invention.

LIST OF REFERENCE NUMERALS 10 magnetic brush
12 microchannel print head
13 printer control circuit
14 receiver electrode
15 stepper motor
16 developer supply
22 rotatable magnetic core
24 stationary outer shell
25 permanent magnetic sectors
26 sump
28 developer
30 magnetic feed roller
32 recording region
34 receiver
36 fusing station
38 blade cleaner
40 microchannel walls
42 microchannels
46 transfer electrode
48 substrate
50 plug
52 conductive trace
54 solder bump
56 IC package tab
58 integrated circuit package
60 SiO2 layer
62 drive circuit
64 logic and control circuit
65 electrical ground
66 power supply
67 bond pad
68 data line
69 insulating/anti-abrasion layer
71 opening
110 cassette
112 pockets
114 vacuum aperture
116 port
118 port
120 cassette
130 transfer station
135 coating
140 medicine or powder
145 coating
150 tablet
160 print heads
162 print heads
181 variable density
410-13 magnetic brushes
415 common axis
510 microchannel print head
610-14 print head assembly
710 print head assembly
720 print head assembly
730 print head assembly

DETAILED DESCRIPTION OF INVENTION

FIG. 1 shows an electrostatic dry powder deposition apparatus according to the present invention. The apparatus includes a magnetic brush generally designated 10, a microchannel print head 12 driven by a control circuit 13 (such as a microprocessor), a receiver electrode 14 driven by a stepper motor 15, and a developer supply 16 for supplying dry pharmaceutical powder to the magnetic brush 10. The stepper motor 15 is controlled by control circuit 13 to synchronize the pharmaceutical powder deposition to the tablet or substrate.

The magnetic brush 10 includes a rotatable magnetic core 22 and a stationary outer cylindrical shell 24. The rotatable magnetic core includes a plurality of permanent magnetic sectors 25 arranged about and extending parallel to the cylindrical surface of the shell 24 to define a cylindrical peripheral surface having alternating North and South magnetic poles.

The developer supply includes a sump 26 for containing a supply of pharmaceutical powder 28, for example, a two component developer of the type having an magnetically attractive carrier and a pharmaceutical powder. A rotatable magnetic feed roller 30 is actuable for delivering developer 28 from the sump 26 to the magnetic brush 10 in a known manner.

The microchannel print head 12 is mounted on the outer surface of shell 24 opposite receiver electrode 14 to define a powder transfer region 32. A substrate 34, such as a pharmaceutical tablet, capsule or other pharmaceutical substrate, is moved through the powder transfer region 32 in the direction of arrow C with one surface in contact with receiver electrode 14. Alternatively, the direction of the receiver and the flow of developer may be in opposite directions. A fusing station 36 may be provided as is known in the art to fuse the pharmaceutical powder to the receiver 34. The fusing station 36 may comprise, for example, a radiant heat source or convection heater.

In operation, the magnetic feed roller 30 is actuated to supply developer 28 to the magnetic brush 10. The developer 28 is transported around the periphery of the magnetic brush 10 to the powder transfer region 32, where pulses are selectively applied to an array of transfer electrodes in microchannel print head 12 synchronized by control circuit 13 to transfer powder from the developer 28 to the receiver 34 in an imagewise manner as the receiver is moved by stepper motor 15 through the recording region 32.

Means are provided on the shell 24 of the magnetic brush 10 such as a cleaning blade 38 so that as the developer is transported around the periphery of the shell 24, it is moved away from the influence of the magnetic core 22 to the point where it falls back into the sump 26.

Figure 2B:
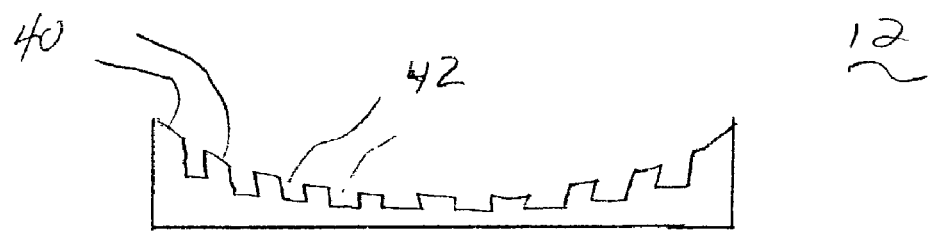
FIG. 2B shows one form of curvature for a print head, to conform to a curved tablet surface.

Referring to FIGS. 2A1, 2A2 a print head 12 according to the present invention utilizes microchannels 42 to control the flow of developer particles and individual transfer electrodes 46 to transfer the powder in pixel wise fashion to a receiver. The print head 12 has a plurality of walls 40 which define a plurality of microchannels 42. Developer particles 28 are caused to travel down the microchannels in the direction of arrow D by the magnetic brush 10. An electrically conducting transfer electrode 46 is located in each of the microchannels. The microchannels can be fabricated on flex material, such as on flex circuit using photoresist to form the channels, or on non-flexible material such as silicon. The microchannel printhead can be formed, for example, by forming the transfer electrodes 46 and conductors (not shown) leading to the transfer electrodes on the surface of the nonflexible material and then applying a photo-imageable polymer to the surface of the non-flexible material and patterning the photo-imageable polymer to form the walls of the channels. The conductors leading to the transfer electrodes may be positioned under the channel walls using this technique. Alternatively, the walls may be formed in the surface by cutting, such as by using a diamond saw or other micromachining techniques known in the art such as wet etching, dry etching, ion milling, laser ablation, and laser cutting. With this approach, the conductors leading to the transfer electrodes may be formed on the back side of the print head and electrical connection made with the transfer electrodes via plated through holes. The microchannels may be machined in any material such as that used as the stationary shell of the magnetic brush. The channel wall height is selected to accommodate the nap height of the developer chains, which depends in turn upon the particular developer and strength of the magnets in the magnetic brush, or upon the height of a leveling skive used to level the developer upon entry into the channels. FIG. 2B shows one form of curvature for a print head to conform to a curved tablet surface.

A print head according to the present invention was prepared by micromachining channels into silicon and mounting the silicon die on the stationary shell of a magnetic brush development station. A flat was machined on the cylindrical shell and the silicon die was mounted on the flat, using an adhesive. A two-component developer with powder particles mixed with magnetic carrier particles was applied to the shell and is transported through the channels in response to the rotating magnet core and toner was transferred to paper in response to an applied voltage on the transfer electrodes.

Microchannels have been fabricated in a silicon substrate with walls ranging from 50 microns to 200 microns. Test results indicate that the higher walls are preferred although both extremes in the range gave acceptable results. The channel length can also be adjusted over a wide range. Channel lengths in silicon and other materials as short as 6 mm and as long as 30 mm have been fabricated and test results indicate that channel lengths in this range are acceptable. The channel width depends upon the required resolution of the printer. A 300 dot per inch printer can be made using 42 micron wide channels separated by a 42 micron thick walls for a channel pitch of 84 microns.

As the magnetic developer particles 28 move along the microchannels in response to the rotating magnetic core 10, they eventually reach the transfer electrodes 46. The transfer electrodes are individually addressable and if zero volts are applied to an electrode, no toner transfer occurs. At applied voltages (plus or minus, depending upon the charge on the toner), toner is transferred to the receiver 34, in proportion to the voltage applied to the electrode 46. Preferably, the transfer electrodes 46 are formed from a non-corroding material such as gold, for example by depositing a layer of electrode material and patterning the material by liftoff techniques.

There are a number of methods known in the art suitable for forming the microchannels, including dry etching, wet etching, cutting, ion milling, laser ablation, etc. The channel width and wall thickness need not have the same dimensions. The wall thickness can be altered independently from the channel width, to accommodate the desired printer resolution. The walls 40 may be provided with an anti-static layer such as indium tin oxide or doped polysilicon to prevent static build-up on the developer particles due to the developer rubbing against the channel walls as it moves through the channels.

Figure 2C:
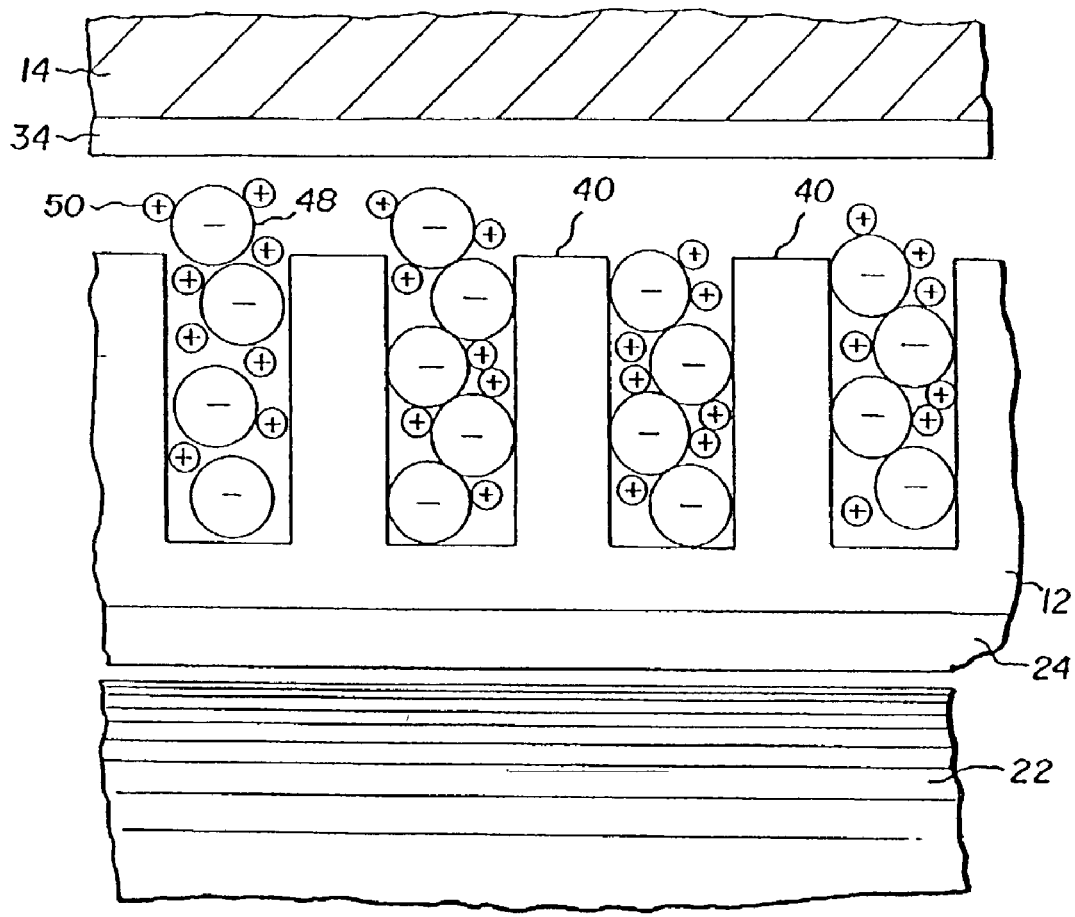
FIG. 2C is a partial cross sectional showing the microchannel print head mounted on the stationary shell of a magnetic brush.
Figure 2D:
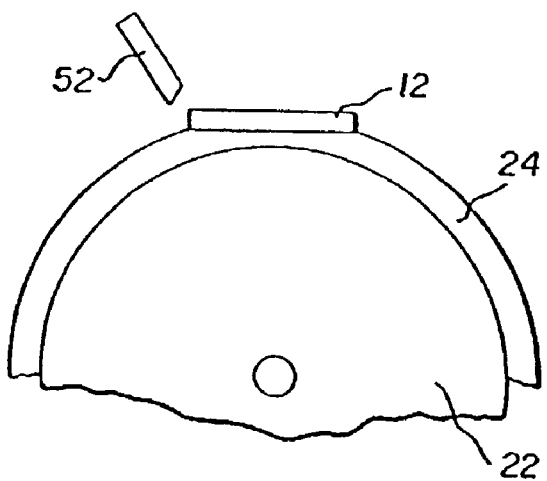
FIG. 2D is a partial side view of electrographic apparatus showing a skive for leveling the developer at the print head.

FIGS. 2C and 2D show the microchannel print head 12 mounted on the stationary shell 24 of magnetic brush 10. The print head 12, made from a rigid material such as silicon is mounted on a flat that has been machined on the shell of the magnetic brush. Other rigid materials such as plastics, thermoplastics, photoresists, etc may be used to manufacture the print head. In a line printer, the print head is at least as wide as the receiver and the row of microchannels extends the entire width of the receiver. Alternatively, a print head that is less than the width of the receiver may be mounted on a carriage and moved across the width of the receiver as is known in the ink jet and dot matrix printer art. In FIG. 2C a dual-component developer having negatively charged magnetic carrier particles 48 and positively charged powder particles 50 is shown flowing through the channels. The print head of the present invention may also be advantageously employed with a single-component magnetic powder.

Alternatively, a dual component magnetic developer with the magnetic carrier positively charged and the insulating powder negatively charged may be employed. Using such a developer, when a negative potential is applied to the transfer electrode 46 at the bottom of the channel, the triboelectric force holding the negatively charged toner to the positively charged carrier particle is overcome causing the toner to leave the carrier and transfer to the paper receiver 34. An opposite charge is induced in the paper drum 14 holding the toner particle to the paper. The amount of toner transferred to the paper 34 is proportional to the potential applied to the transfer electrode 46. Toner is transferred when a chain of developer particles 28 contacts the transfer electrode 46. No toner transfer occurs for developer chains not in contact with the transfer electrode 46.

At the transfer electrode 46, the height of the developer in the channel is preferably about the same or greater than the height of the walls 40. It is also possible to print with the developer height less than the microchannel wall height by employing the technique known as projection development to cause the toner particles to transit a gap between the print head and the receiver. As shown in FIG. 2D, the developer height can be controlled with the use of a skive 52 located at the entrance to the print head 12. Both magnetic and non-magnetic leveling skives are known in the art for providing an effective means for controlling developer nap height. Although it is preferable to place the skive near the entrance of the microchannels, its exact placement is not critical.

Figure 2E:
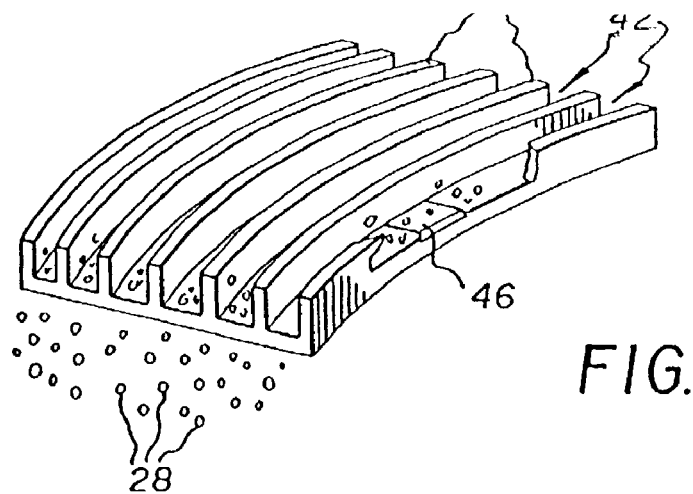
FIG. 2E is a partial perspective view showing a curved microchannel print head.

FIG. 2E shows a curved microchannel print head 12. The curved print head 12 can be made from flexible material such as photoresists, solder mask, etc. The print head 12 can be mounted on the stationary shell 24 by shaping the head to the shell contour and attaching the print head to the shell, for example, by an adhesive. Alternatively, the curved print head 12 may be made from a non-flexible material such as a ceramic material that is formed with the curved shape and cured to have the same curvature as the stationary shell 24.

Also shown in FIG. 2E are developer particles 28 flowing in the microchannels in response to the rotating magnetic core 22. Prior to reaching the microchannels 42, the developer 28 uniformly spreads out across the shell. As the developer enters the microchannels 42, it is confined to move in one or another of the channels and, upon reaching the transfer electrode 46 located in the channel, can be selectively transferred to a receiver sheet. The transfer electrodes 46 may be placed anywhere inside of the channel.

Figure 2F:
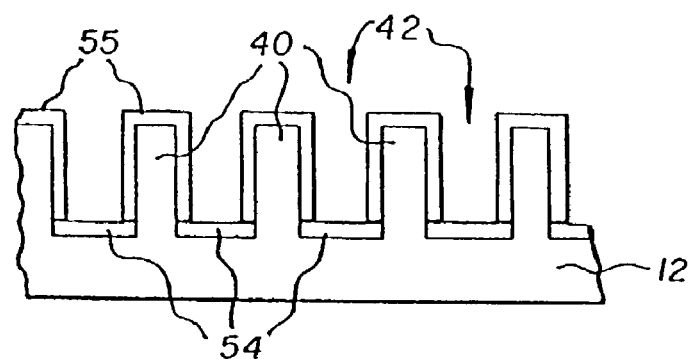
FIG. 2F is a partial cross sectional view of a microchannel print head having magnetic permeable strips on the bottom of the channels and an anti-abrasion layer on the channel walls.

As shown in FIG. 2F strips of magnetic permeable material 54 may be provided on the bottom of the channels to further confine the magnetic developer to the channels, thereby further reducing channel crosstalk. The magnetic permeable strips 54 may also be located external to the microchannels to pre-form developer ridges which aid in the developer flow as it enters the channels. Such external magnetic permeable strips can be used as an alternative to or in combination with the other features described below to assist in the developer flow as it enters the microchannels. The magnetic strips 54 are electrically insulated from the transfer electrodes 46. Alternatively the magnetic strips may function as both the transfer electrodes and the conductors to the transfer electrodes by providing a dielectric covering over the strips with a window in the dielectric at the location of the transfer electrode.

The magnetic carrier particles are made of ferrites which can be very abrasive. Since the receiver sheet is closely spaced to the tops of the channel walls 40, developer particles may become entrained between the channel tops and the receiver sheet and abrade the tops of the channel walls. To address this problem, an anti-abrasion layer 55 such as silicon nitride or silicon carbide may be formed on the tops and/or on the sides of the channel walls 40 to prevent abrasion from the developer particles. A layer of partially conductive diamond-like carbon may provide both antistatic and anti-abrasion properties.

Figure 2G:
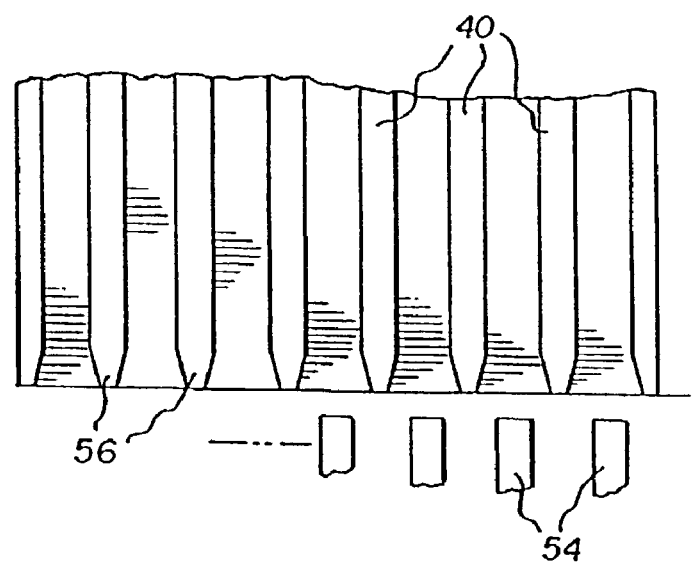
FIG. 2G is a partial top view of the microchannel print head, having tapered entrances to the microchannels.

As shown in FIG. 2G the ends 56 of the walls 40 at the entrance to the microchannels may be tapered to "funnel" the developer into the channels. The tapered channels improve the developer flow into the channels by providing a gradual entrance to the channel. In addition, the magnetic permeable strips 54 may be provided external to the tapered microchannels to pre-form developer ridges that will aid in the developer flow as it enters the tapered channels.

Figure 2H:
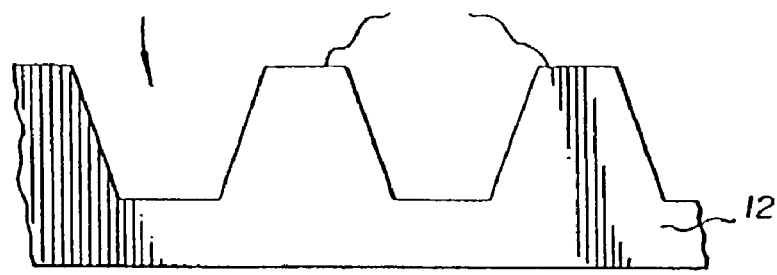
FIG. 2H is a partial cross sectional view of a microchannel print head having outwardly sloping channel walls to improve toner flow.
Figure 2I:
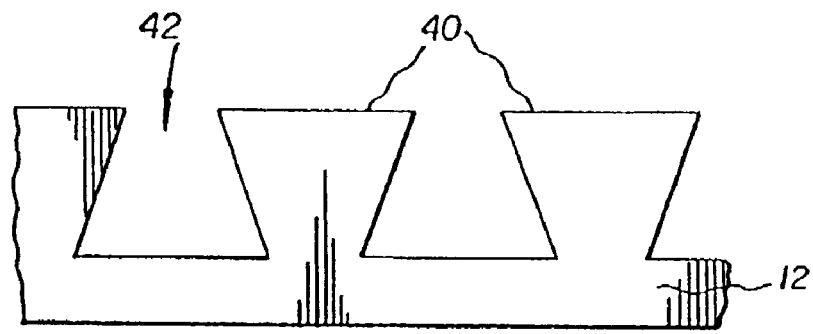
FIG. 2I is a partial cross sectional view of a microchannel print head having inwardly sloping channel walls to improve resolution.

As shown in FIG. 2H, the channel walls 40 may be sloped so the channels 42 are wider at the top than at the bottom to improve developer flow in the channels. The channel walls may have a vertical portion at the bottom of the channel and slope near the top. The top of the channel wall may diminish in width sufficiently to define a knife edge. The rate of slope may continuously change so that the sides of the walls are curved from top to bottom. Alternatively, as shown in FIG. 2I, the channel walls 40 may be oppositely sloped to improve resolution of the print head.

Figure 2J:
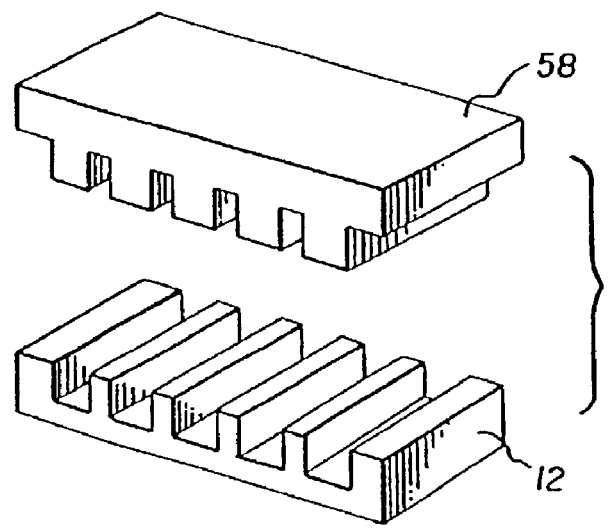
FIG. 2J is a schematic diagram illustrating the production of a microchannel print head by stamping from a master.

As shown in FIG. 2J, the print head 12 may be formed by stamping from a master 58 produced for example by laser machining, to produce a microchannel print head 12. Stamping from a master can be used to form a print head from flexible materials that may be bent to conform to the cylindrical shell 24 of the magnetic brush 10 or may be used to form a print head using ceramic material that can be curved or planar.

Figure 2K:
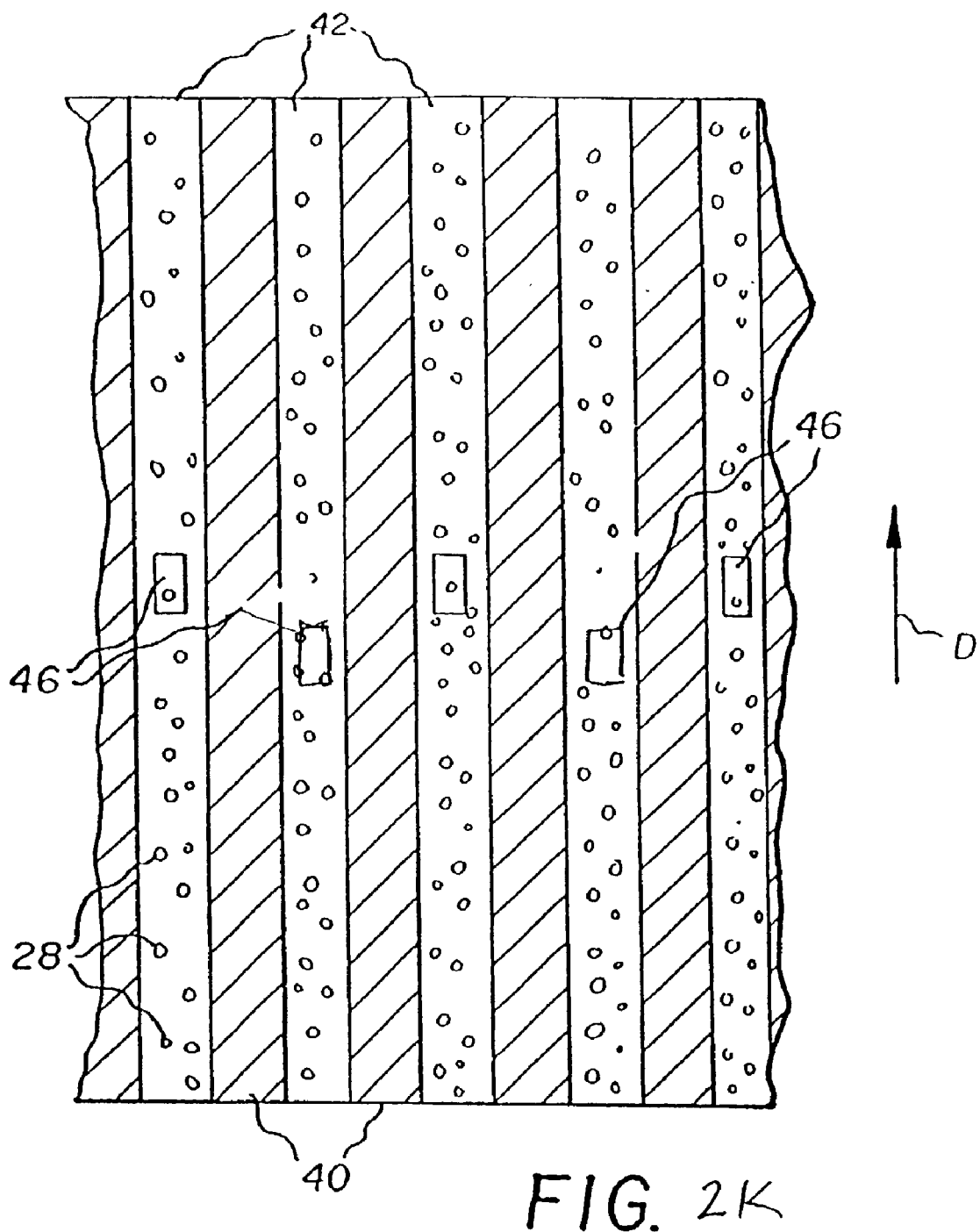
FIG. 2K is a partial top view of an alternative embodiment of the print head of the present invention, having staggered electrodes.

Referring to FIG. 2K, according to an alternative embodiment of the present invention, the transfer electrodes 46 in the microchannels 42 may be staggered to further reduce crosstalk between the channels.

Figure 3:
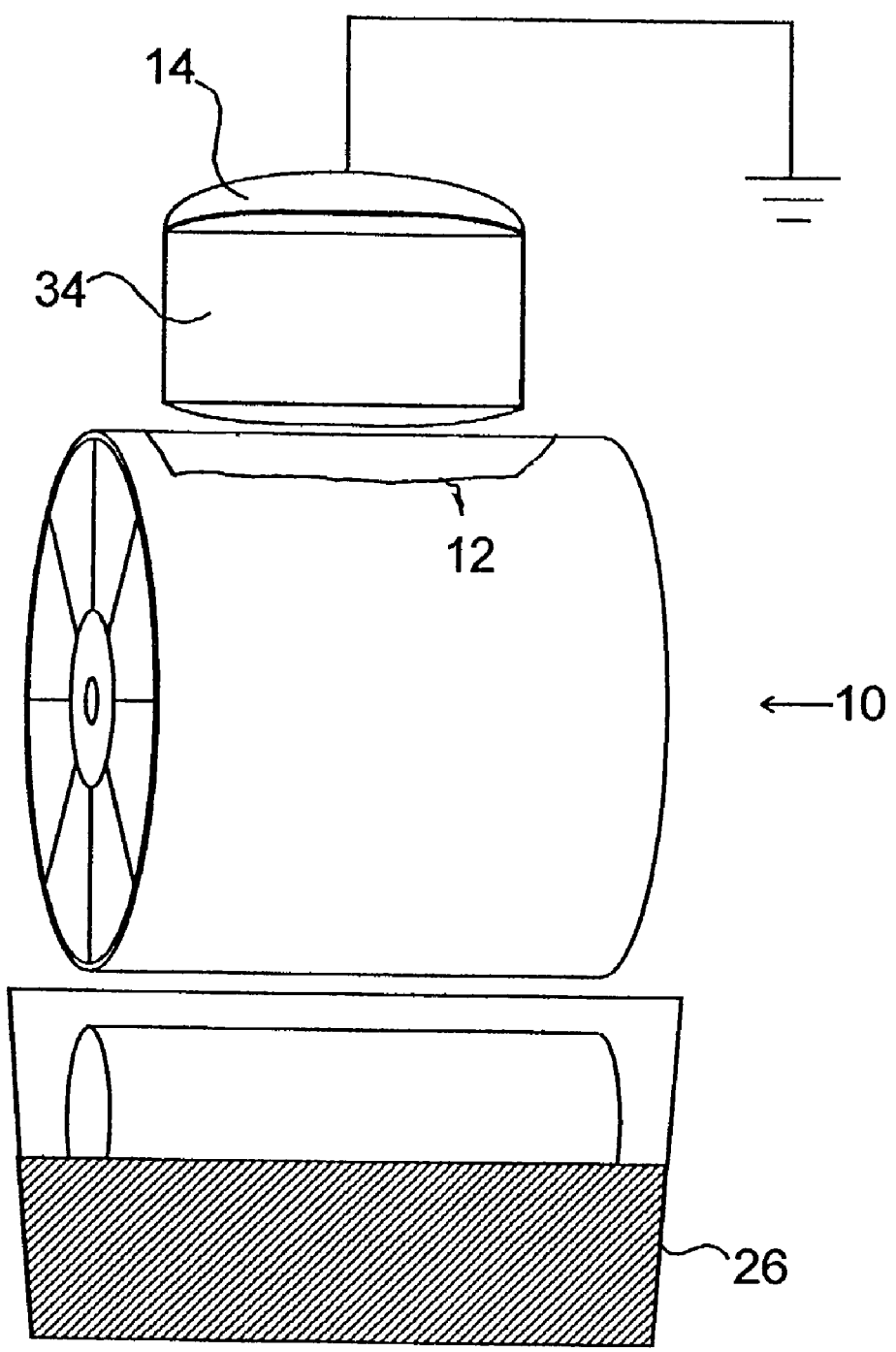
FIG. 3 illustrates a tablet moving over a microchannel print head mounted on a stationary shell of a rotating multipole magnetic brush development station. The width of the print head is slightly larger than the tablet to accommodate coating of the sides of the tablet.

FIG. 3 illustrates the elements of an exemplary electrostatic dry powder deposition apparatus. A tablet is held in position by a conductive vacuum suction cup serving as the receiver electrode, a technique well-known in the art. Both conductive and nonconductive tablets can be coated in this manner. If the tablet is conductive, the counter charge corresponding to the voltage applied between the conductive cup and the transfer electrode in the microchannel resides on the tablet surface facing the print head. If the tablet is insulating, the counter charge resides on the suction cup.

In an insulating tablet, part of the applied voltage is dropped across the tablet. Consequently, in order to deposit the same amount of powder on the tablet surface as for a conducting tablet, the voltage pulse applied to the transfer electrode in the microchannel must be correspondingly higher than for the conducting tablet. In either case, the powder can be deposited in a specific area of the tablet by applying a voltage to the transfer electrode in the corresponding microchannel. To totally cover one surface and the sides of the tablet all transfer electrodes in each of the microchannels would be activated.

Figure 4:
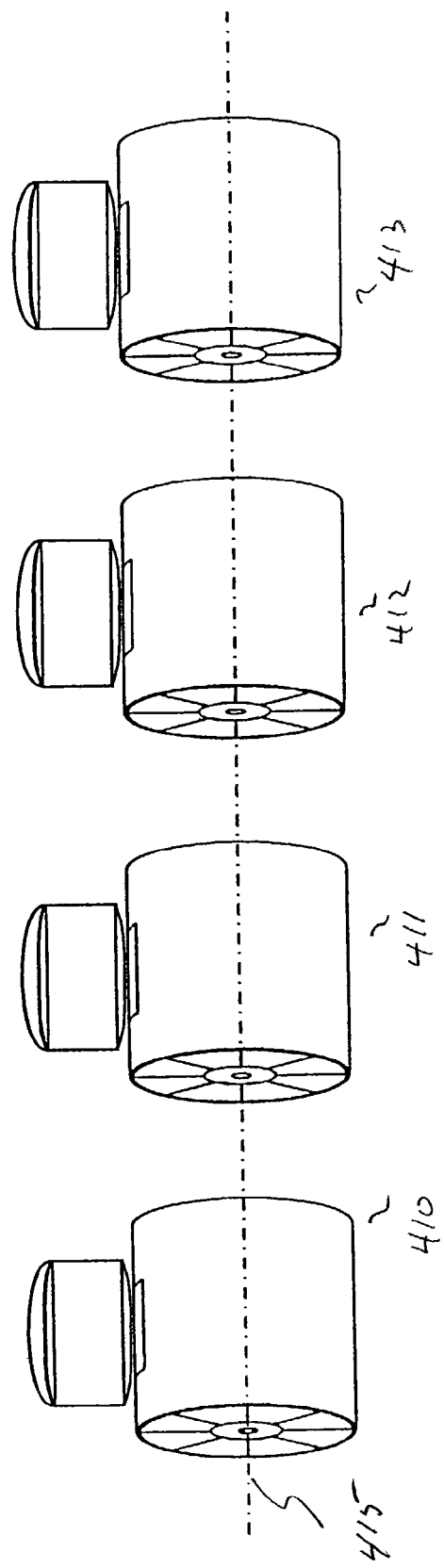
FIG. 4 shows a number of print heads each with its corresponding multipole magnetic brush mounted on a common axis.

FIG. 4 shows a configuration for depositing pharmaceutical powder on an array of tablets. There may be a separate sump for each of the multipole magnetic brushes 410-13 or a single sump for supplying the entire array of print heads with developer. Each magnetic brush and print head are mounted on a common axis 415 to ensure constant spacing between the print head and the tablet. Segmenting the magnetic core into a number of smaller magnets reduces the torque required of the motor that rotates a single magnet extending the entire length of the coating apparatus. Also it is less costly to manufacture and magnetize magnets of shorter length than a single magnet which extends the entire length of the coating apparatus.

Figure 5:
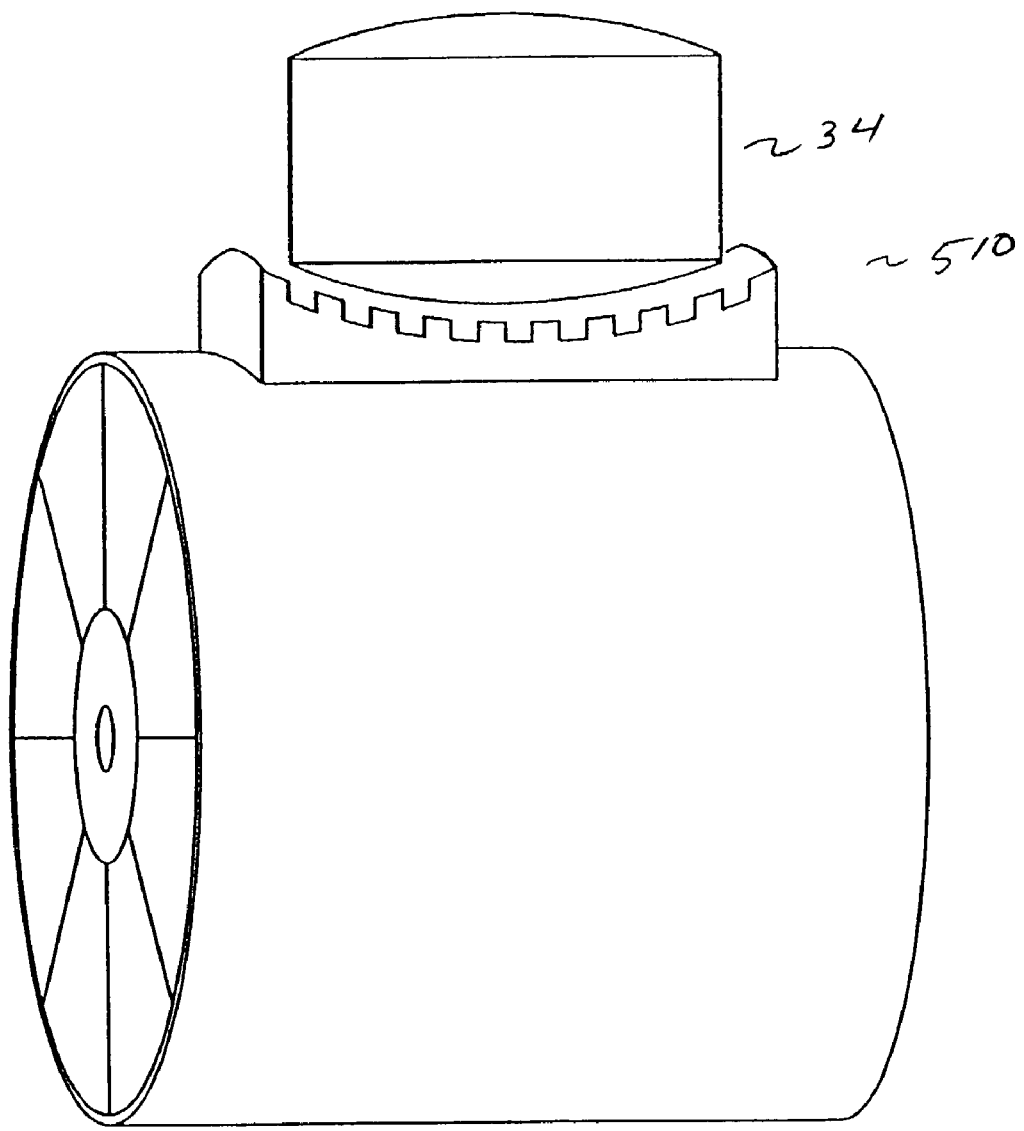
FIG. 5 illustrates a microchannel print head with surface contours corresponding to the tablet curvature.

FIG. 5 shows a microchannel print head 510 with a surface profile that conforms to the shape of the capsule being coated. In this configuration a more uniform coating can be obtained since, in general, the powder thickness depends upon the spacing between the substrate and the print head for a given time. It is understood that the amount of deposited material depends upon the duration of the tablet proximate the microchannels and thus is inversely proportional to the relative speed of the tablet with respect to the microchannels.

Figure 6:
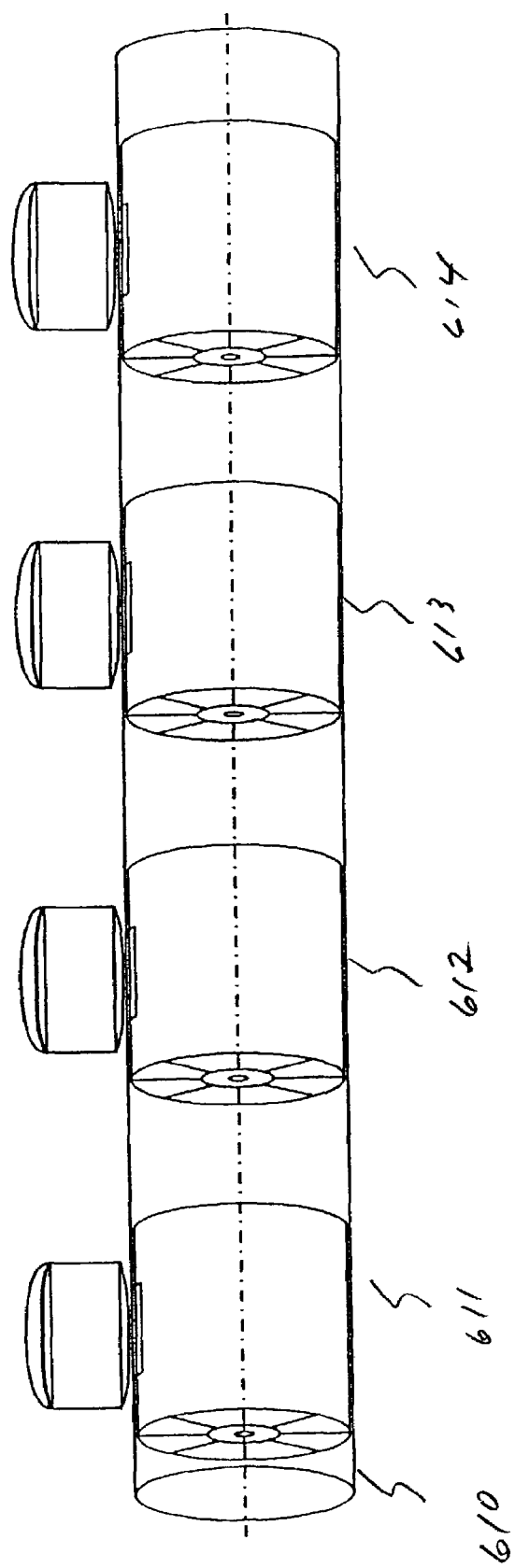
FIG. 6 shows a single stationary shell with segmented coaxial multipole magnetic cores and corresponding equal number of microchannel print heads arranged along the shell's cylindrical length.

FIG. 6 illustrates using a single stationary shell whose length is a multiple of the desired substrates needed to be coated. A print head assembly, in which the length of each print head matches the substrate size 610-14, is mounted linearly along the length of the shell with a gap between each print head. In this manner, since the print head can be only a few millimeters in length, the fabrication process is much simpler and less costly than making a print head whose length is the same as that of the shell. Not only is the fabrication simpler, but the integrated circuits required to drive the print head is far easier to produce. The number of print heads obtained from a single wafer would be far greater than that obtained for a page width print head.

Figure 7:
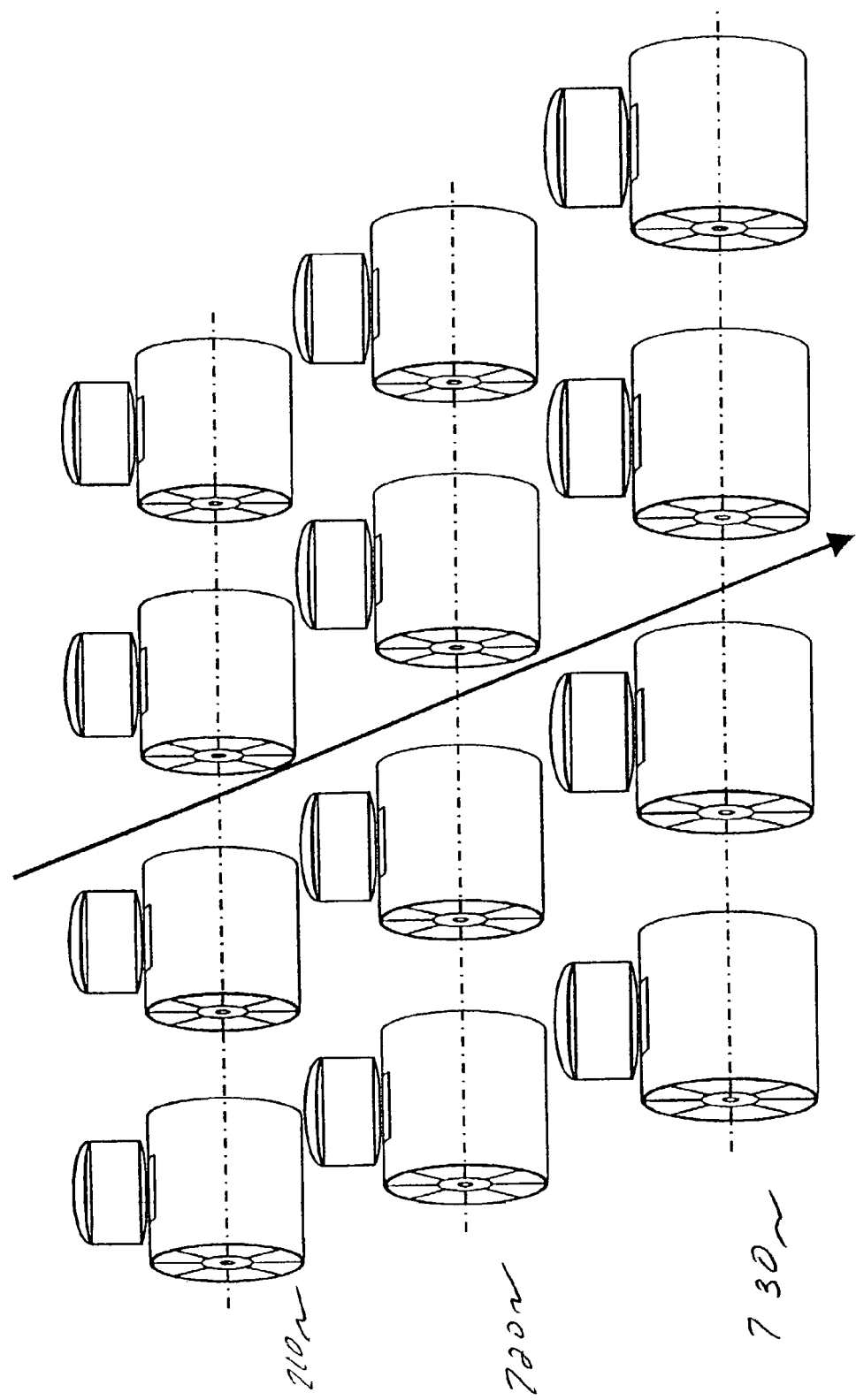
FIG. 7 shows several print head assemblies each with a different type of powder for multiple powder deposition on a single side of the tablet.
Figure 8:
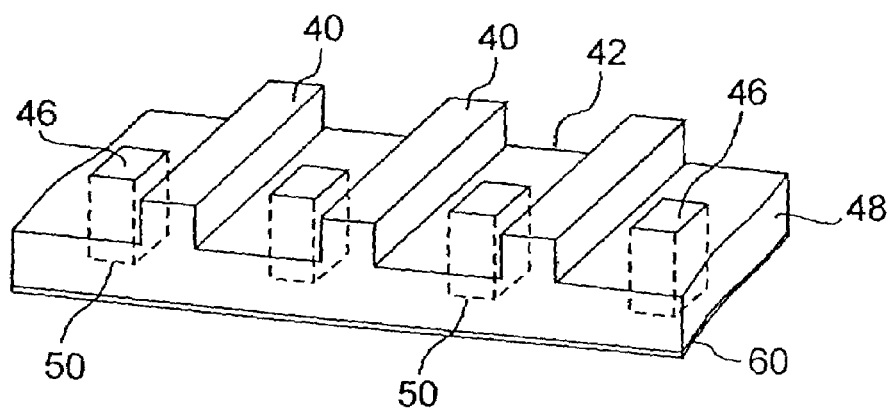
FIG. 8 is a partial perspective view of the substrate of a microchannel print head according to one embodiment of the present invention.

See FIG. 7 for an array of print heads for multi-layer printing. The arrow shows the direction of movement for tablets being printed. In this form of the invention, a single tablet may pass through multiple print heads for pharmaceutical deposition, printing, coloration, or other added layering of substances as needed. With the array of print heads 710, 720, 730, one may coat tablets with multiple colors to form images, alphanumeric characters, bar codes, logos or other graphic representations. The arrays can also apply multiple layers of the same or different coatings to the tablets.

Any commercial realization of the print head must take into account the associated drive/control electronics and the wiring that connects the drive electronics to the transfer electrodes. A constraint of any connection scheme is that there must be no interference with the flow of developer particles. In the example of a 300 dpi print head one inch wide, there are at least 300 individual transfer electrodes. Each microchannel may have one or more transfer electrodes. If multiple print heads are assembled side by side along the axis of the magnetic core drive shaft to process multiple substrates, the large number of electrodes makes it difficult to form conductive paths that lead out to the lateral-edges of the print head while still maintaining the short length (in the direction of developer travel) of the print head.

Print Head Shaping

The integrated microchannel print head of the present invention can be constructed in a number of ways. According to one approach, the microchannels are formed using an additive process by applying a layer of material onto the substrate and patterning the added layer to form the channels. Additive processes may include coating, epitaxial growth, deposition, lift-off and bonding, printing and possibly subsequent patterning of the added layer. A presently preferred additive technique for forming microchannels is to pattern a thick photoimageable polymer, such as novalac photoresist or a polyimide, using standard photolithographic techniques.

In another approach the microchannels are formed using a subtractive process by removing material from the substrate to form the channels. Subtractive processes can include techniques such as etching, sawing, ion milling, electrodischarge machining, and laser cutting. A preferred technique is fast anisotropic etching into the bulk of a silicon substrate using conventional high density plasma etching techniques for silicon. The drive and control circuitry may be provided either in the form of microelectronic circuits integrated on or into the substrate or as hybrid electronic chips bonded to the substrate.

Electrode Formation

One embodiment of the integrated microchannel print head is shown in FIGS. 8-11. Microchannels 42 are formed on a silicon substrate 48 by either an additive or subtractive process. Electrical connection to the transfer electrodes 46 are formed by via plugs 50 from the bottoms of the microchannels 42 to the opposite side of the silicon substrate. In a presently preferred embodiment, the tops of the via plugs 50 function as the transfer electrodes. Alternatively, a transfer electrode may be formed over the top of, and in electrical contact with, the via plug 50.

Via plugs 50 can be formed using conventional electroplating techniques. A preferred method is to attach an electrically conductive, passivated backer plate to the substrate surface opposite the microchannels 42. All surfaces of the substrate 48 are covered with an insulating material, for example, a thermal or plasma-enhanced chemical vapor deposited (PECVD) silicon dioxide layer. When immersed in an electroplating bath, deposition is initiated only on the portions of the backer plate exposed at the bottoms of via plug cavities. The electroplating process is conducted in a timed fashion so that the plated material completely fills the via plug cavity, forming the via plugs 50. As is known in the art, the passivation on the backer plate surface provides adequate electrical conductivity for the electroplating process but does not adhere well to the plated material. Thus, the wafer can be separated from the backer plate without damage by simple mechanical means. Note that the via plugs 50 are electrically insulated from the substrate 48.

Logic and Control Circuit Structure and Connection

Figure 9:
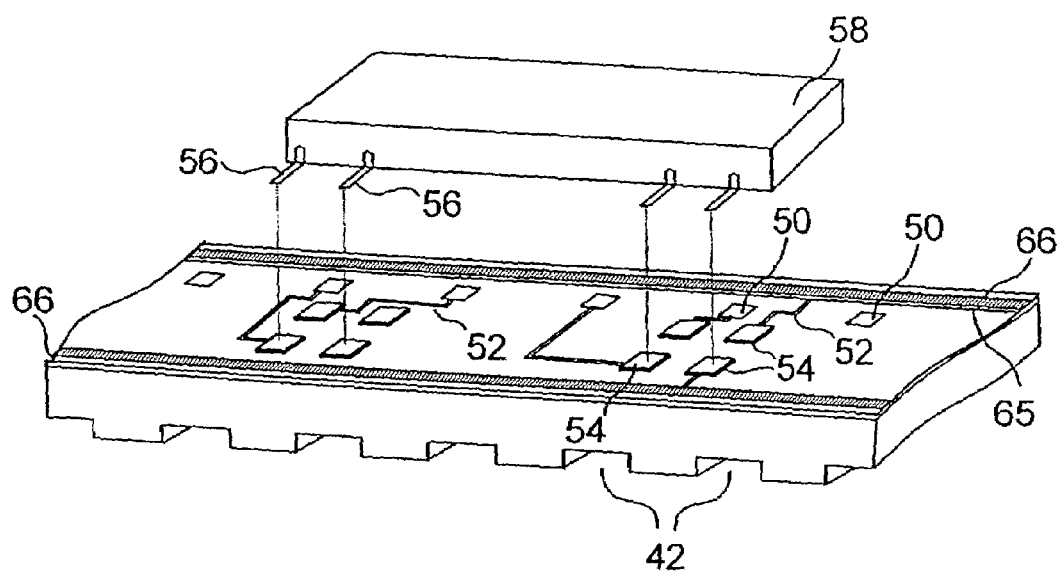
FIG. 9 is an exploded partial perspective view of a microchannel print head shown in FIG. 8.
Figure 10:
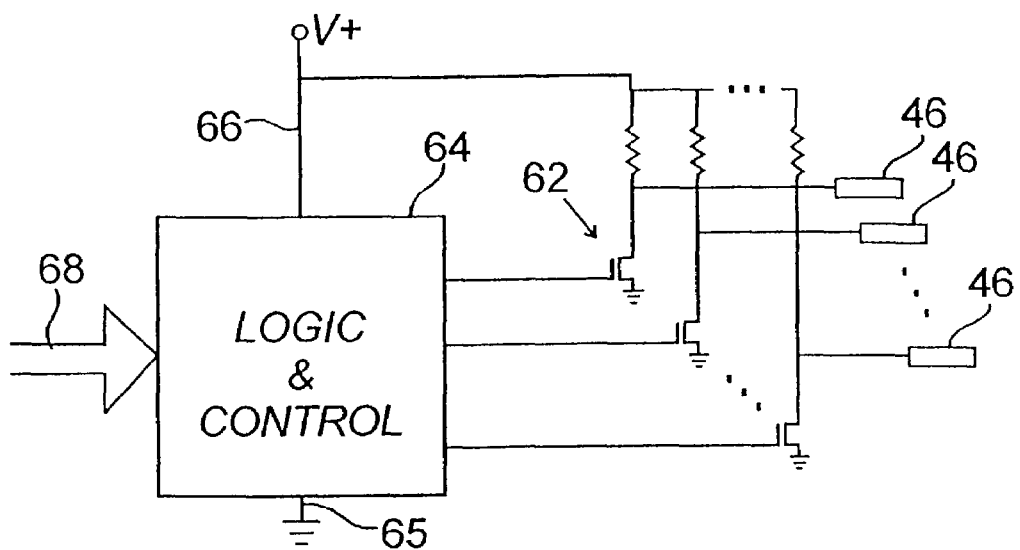
FIG. 10 is a circuit diagram showing the logic and control circuitry and drive circuits employed with the microchannel print head shown in FIG. 8.
Figure 11:
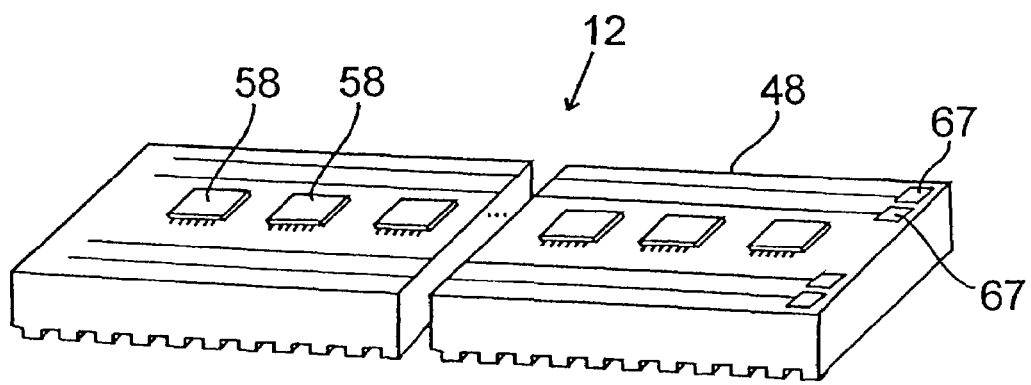
FIG. 11 is a partial perspective view showing the bottom side of a completed microchannel print head shown in FIG. 8.

Referring to FIG. 9, conductive metal traces 52 are provided to connect the bottoms of the via plugs 50 to a set of solder bumps 54 that are configured in a geometry that matches the tabs 56 of a standard surface mount integrated circuit package 58 that contains drive circuitry for the transfer electrodes. Alternatively, the circuits may be packaged in flip-chips and the solder bumps 54 provided on the substrate 48 in the appropriate pattern for attaching the flip chip to the substrate. The conductive metal traces 52 and the solder bumps 54 are insulated from the substrate by a layer of silicon dioxide 60. As shown in FIG. 10, the integrated circuit packages 58 will typically contain a number of individual drive circuits 62 (for example, 32, 48, 64, or 128 separate drive circuits) and additional logic and control circuitry 64 for, decoding, timing, and other functions. Suitable integrated circuit packages containing drive circuits and logic and control circuitry are available as "High Voltage Driver/Interface ICs" e.g. HV03, HV34, HV622, etc., from Supertex Inc., Sunnyvale, Calif. A number of bus lines are provided along the back of the print head to supply each integrated circuit package 58 with electrical connections. These would include electrical ground 65, power supply 66, and data lines 68 for carrying the digital input signals from printing control circuit 13 that represent the image to be printed. As shown in FIG. 11,
bond pads 67 are provided on the back of the substrate 48 for external electrical connection to the bus lines. As shown in FIG. 11, the number of electrical conductors 67 is fewer than the number of transfer electrodes 46 in channels 42.

In the example of a one-inch 300 dpi print head suitable for transfer of material to tablets, a minimum of 5 integrated circuit packages 58 each having 64 drive circuits may be used. The circuit packages or drive chips 58 are tiled along the back of the print head 12 forming a single integrated assembly, as shown in FIG. 11. Note that in this embodiment it is convenient but not necessary to use silicon as the substrate. Since no aspect of this embodiment makes use of silicon's properties, any other suitable material could be used. For example, a ceramic substrate such as that used for integrated circuit packages, plastic, glass, or a printed circuit board material such as glass loaded epoxy may be used as the substrate material.

Figure 12:
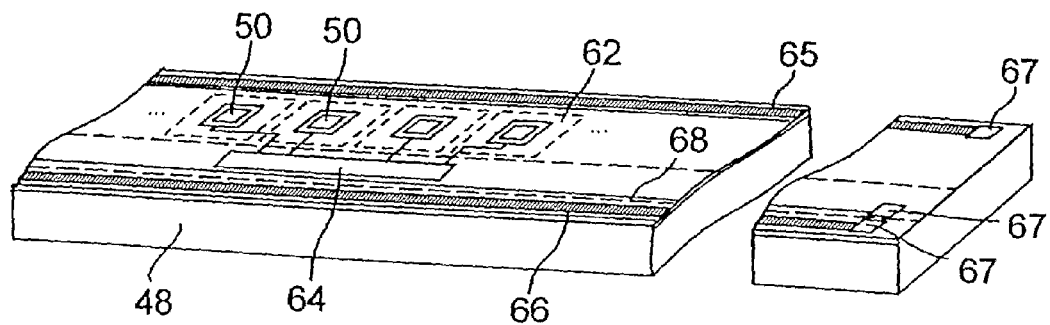
FIG. 12 is a partial perspective view of the substrate of a microchannel print head according to an alternative embodiment of the present invention.
Figure 13:
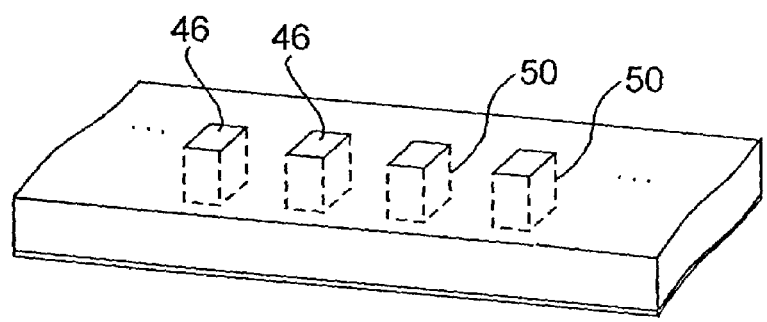
FIG. 13 is a partial perspective view showing the top of substrate shown in FIG. 12.
Figure 14:
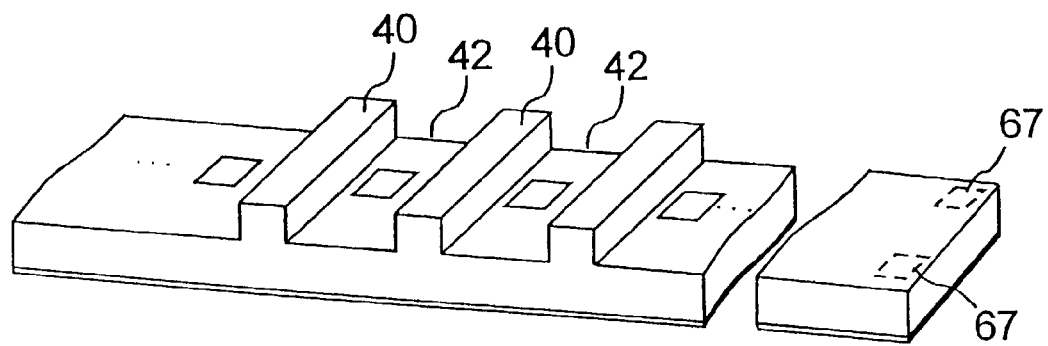
FIG. 14 is partial perspective view of the completed microchannel print head shown in FIG. 12.

Another embodiment of the integrated microchannel print head according to the present invention is shown in FIGS. 12-14. Microelectronic circuitry including the drive circuits 62 adjacent to the bottom surfaces of the via plugs 50 and the logic and control circuitry 64 connected to the driver circuits 62, is first formed on the bottom surface of a silicon substrate 48 as shown in FIG. 12. Note that the bottom surface of the substrate 48 shown in FIG. 12 will become the bottom surface of the print head 12. Each individual drive circuit 62 provides a voltage to a single transfer electrode 46 through a via plug 50. As shown in FIG. 12, the number of electrical conductors 67 are fewer than the number of via plugs 50 connected to transfer electrodes 46.

The voltages required for proper operation of the microchannel print head 12 are typically in the range 50-200 volts. A microelectronic fabrication technology such as high voltage complementary metal oxide semiconductor (HVCMOS) or doubly diffused metal oxide semiconductor (DMOS) is employed to obtain such voltages. The pitch of the individual drive circuit channels matches the desired pitch of the print head. The via plugs 50 are arranged in such a geometry that there is back-to-front correspondence of the via plugs 50 and the intended positions of the transfer electrodes 46. Logic and control circuitry 64 is arranged along one or both edges of the print head. A number of bus lines are provided along the back of the print head to supply each integrated circuit 62 and 64 with external electrical connections. These would include electrical ground 65, power supply 66, and data lines 68 for carrying the digital input signals from printing control circuit 13 that represent the image to be printed. Bond pads 67 are provided on the back of the substrate 48 for external electrical connection to the bus lines. Logic and control circuitry 64 can be formed using a standard fabrication technology such as CMOS. Control, decoding, timing, and other functions are performed by this circuitry. The substrate 48 with the integrated circuitry formed on it can be purchased from a foundry that specializes in application specific integrated circuits (ASICs). This reduces the capital requirements needed to build integrated microchannel print heads according to the present invention.

The transfer electrodes 46 and via plugs 50 are formed as shown in FIG. 13, as described above. The alignment of the transfer electrodes 46 and via plugs 50 with respect to the drive circuits 62 is accomplished by suitable lithographic techniques such as infrared alignment or front-to-back alignment. Referring to FIG. 14, microchannel walls 40 are formed on the top side of the substrate 48 by one of the additive techniques noted above.

Figure 15:
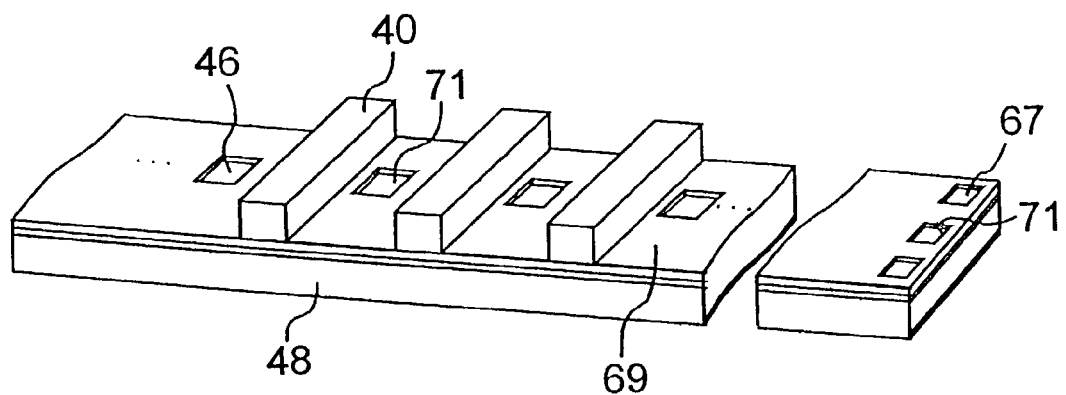
FIG. 15 is a top partial perspective view of a further alternative embodiment of a microchannel print head according to the present invention.

See FIG. 15 for an alternative method of forming a microchannel print head according to the present invention. This method starts with a substrate 48 similar to that shown in FIG. 12 with multiple individual drive circuits 62 and logic and control circuitry 64. Rather than forming via plugs 50, a series of transfer electrodes 46 are formed as a part of the drive circuits 62. In this embodiment, the surface of the substrate containing the circuitry is considered the top surface of the substrate 48. An insulating and/or anti-abrasion layer is formed on the top surface of the substrate 48 so as to protect the microelectronic circuitry. Openings 71 are formed in the insulating/anti-abrasion layer 69 to expose the transfer electrodes 46 and bonding pads 67. A suitable insulating/anti-abrasion layer 69 is provided by a PECVD silicon dioxide or silicon nitride that is patterned using standard photolithographic and etching techniques. A completed print head 12 is formed, as shown in FIG. 15, by adding microchannels walls 40 through an additive technique such as thick photoimageable polymer processing as discussed above.

Another embodiment combines the plastic microchannel structure in the first embodiment with a single, connected silicon-based integrated-circuit sheet, joined to the electrodes by solder-bump technology. In this embodiment the curvature of the print head does not affect the circuit fabrication.

In another range of embodiments, the invention incorporates multiple transfer electrodes in each microchannel, forming a matrix of electrodes and facilitating finer control over the amounts of material deposited in a single pass over a tablet.

In all embodiments, the invention incorporates a system of measurement of the electric current used in the deposition process for each transfer electrode. This facilitates a precise determination of the amount of material deposited with each pulse to an electrode.

Tablet Shape and Print Head Traversal

Figure 16A:
FIGS. 16a through 16g show different tablet (substrate) forms to be processed.
Figure 16B:
Figure 16E:
Figure 16C:
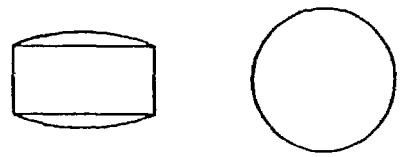
Figure 16F:
Figure 16G:
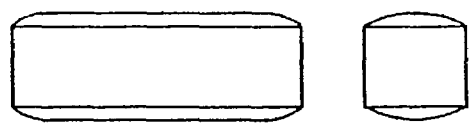
Figure 16D:
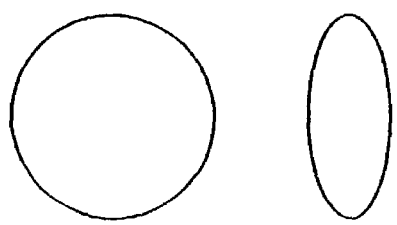

Different tablet shapes require different forms of traversal for the print head. The most common shapes include these cases:

a) disk-shaped tablets with flat faces, like stubby cylinders (see FIG. 16a);
b) disk-shaped tablets having flat faces beveled or curved at the edges (see FIG. 16b);
c) disk-shaped tablets with spherically convex faces, like aspirin (see FIG. 16c);
d) tablets in oblate spheroid shape, like a flattened ball (see FIG. 16d);
e) tablets in prolate spheroid shape, something like a football (see FIG. 16e);
f) cylindrical tablets or capsules with spherically-rounded ends (see FIG. 16f);
g) elongated tablets with cylindrically-convex faces and rounded ends (see FIG. 16g); and
h) spherical tablets.

The print head's transfer electrodes must remain at substantially the same distance from the tablet regardless of the shape of the tablet during all printing operations. This constancy of distance insures proper delivery of payload to the tablet surface, and proper adhesion of that payload once it is delivered. It is not considered necessary to deliver payload to all surfaces of a tablet.

For the flat-faced tablet of a), the print head may be passed over it in a straight line, at a constant distance. If no printing is required on the edge-beveled regions of the tablets of b), the same holds true in that case. A tablet or capsule with a cylindrical surface, such as the tablet of f), may be rotated about its cylindrical axis to present a constant distance to the print head. In this usage, no printing is required for the spherical ends of such a tablet. An elongated tablet with cylindrically-convex faces and rounded ends, such as the tablet of g), may be rotated around the cylindrical axis of each face. For cases a), b), f), and g), a print head having its electrodes in a straight line is incorporated in a first set of embodiments of the print head movement mechanism.

Because cases f) and g) have cylindrical surfaces, they may also be printed using a print head with a curved profile of electrodes. The printing is done by passing the print head the length of the cylindrical surface in a straight line, paralleling the axis of the cylinder. This constitutes a second set of embodiments of the print head movement mechanism.

Because cases c), d), e), and h) are doubly-curved, meaning that they show surface curvature in two dimensions, they present a different problem for the print head. Any rigid print head passing linearly (in a straight line) over a doubly-curved surface will have one or more of its transfer electrodes farther from the surface at some times than at others during the traversal. This is undesirable because the varying distance to the surface leads to variation in the amount of payload deposited on different parts of the surface at a given time. Linear movement of the print head must be restricted in its use to the flat surfaces of the tablets of a) and b).

A third set of embodiments of the print head movement mechanism uses a print head with a curved profile, meaning that its electrodes are not in a straight line. In this embodiment, the print head follows a curved (non-linear) path around the spherical surface of the tablet. This is done either with a moving print head passing the tablet, or with a tablet turning to present different parts of its surface to the print head. In either case, the path of the moving component past the stationary component describes a circular arc with a radius of curvature substantially equal to the radius of the spherical curvature of the tablet surface. Due to the print head's curved profile, there is some loss in speed of surface traversal of the print head at its edges, but this difference in speed is not significant. The radius of spherical curvature of the surface is most likely at least several times the tablet thickness, making the differences in speed fairly small. These embodiments addresses cases c), d), e), and h).

To summarize, the following embodiments are provided for the print heads and the chucks that hold the tablets being printed:

1. A stationary-tablet, flat-print head, linearly-moving-print head design, to cover cases a) and b);
2. Alternatively to 1, a linearly-moving-tablet, flat-print head, stationary-print head design, to cover cases a) and b);
3. A rotating-tablet, flat-print head, stationary-print head design, to cover cases f) and g), wherein the tablet rotation is around the tablet's cylindrical axis for case f), or around the cylindrical axis of revolution of the surface being printed for case g);
4. Alternatively to 3, a stationary-tablet, flat-print head, revolving-print head design, to cover cases f) and g), wherein the print head revolution is around the tablet's cylindrical axis for case f), or the cylindrical axis of revolution of the surface being printed for case g);
5. A rotating-tablet, curved-print head, stationary-print head design, to cover case c), wherein the tablet rotation is around the center of the spherical surface, on a plane through the tablet center;
6. Alternatively to 5, a stationary-tablet, curved-print head, revolving-print head design, to cover case c), wherein the print head revolution is around the center of the spherical surface, on a plane through the tablet center.

7. A rotating-tablet, curved-print head, stationary-print head design, to cover cases d) and e), wherein the tablet rotation is around the sole axis of symmetry of the prolate or oblate surface; and 8. Alternatively to 7, a stationary-tablet, curved-print head, revolving-print head design, to cover cases d) and e), wherein the print head revolution is around the sole axis of symmetry of the prolate or oblate surface, on a plane through the tablet center. The production of tablets may permit using 1 or 2 on flat tablets of cases a) and b), which will later be built up through successive depositions into non-flat shapes such as those in c)-f). Such a possibility makes the simpler approaches of 1 and 2 more widely useful.

The cases and embodiments of the print head movement mechanism described above are exemplary but not restrictive. Using further combinations of relative movements and positionings of tablet and print head, additional sets of embodiments may be constructed by one of ordinary skill in the art to meet the requirements of the cases listed above and cases such as: i) tablets with surfaces having non-spherical two-dimensional curvature and j) polyhedral tablets with rounded edges. Repeated passes of one or more print heads over the surface of a tablet may be used to print on any part of its surface or provide color or other layering to any area of its surface.

Tablets may have surface treatments to present pits, holes, grooves or other textures to the invention. While discrete layering of drugs on tablets is envisioned, nothing bars the invention from working with deposits which work as implants on the substrate tablet.

Range of Deposited Substances

The invention's print head may deposit drugs, protective coatings, inks for text, logo, or bar code display, or other pharmacologically-safe substances having other functional properties. Such substances include those providing aroma or taste, those adding tactile texture to the surface to assist visually-impaired users, and those imparting active chemicals which change color or other obvious aspect of appearance to inform user of possible change in drug composition due to heat, humidity, age, or other factors.

The invention opens up possibilities in still-evolving technologies. It can be used to deposit harmless organic semiconductors in patterned layers to create bioelectronic circuits. This opens up a new realm of programmed pharmaceuticals. Such pharmaceuticals can react differently to different conditions of ingestion, such as acidity level, presence of certain specific ions, or other biochemical conditions. An illustration would be a tablet containing its own deposited battery, circuitry, and medication. On ingestion, the tablet would react with digestive fluids to activate the battery and the printed-on circuits. On detecting certain ions, the circuitry might initiate a process of deactivation or transformation of the accompanying medication, thereby protecting the user from a possibly harmful interaction. The battery and circuitry would then be digested or eliminated through normal bodily processes.

The invention has been described with reference to a preferred embodiment. However, it will be appreciated that variations and modifications can be effected by a person of ordinary skill in the art without departing from the scope of the invention. For example, although the invention has been described showing only one transfer electrode per channel, each channel may be provided with a plurality of transfer electrodes and angled microchannels. Also as an example, the invention's print head has been described showing only linear and circular movement relative to the tablet or other substrate, but the print head may be mounted in an arm or other device driven by fine-resolution stepping motors for creating other relative trajectories of movement.

Two Sided Coating

The invention also enables the user to coat tablets on both sides. In order to do this the tablets can be manually repositioned within the holding chuck. However, as an alternate and more efficient method and apparatus, the invention provides tablet array chucks that hold multiple tablets so that the tablets can be coated on one side and then reversed for coating on the opposite side. Examples of this feature of the invention are shown in FIG. 17A-17H. The tablets 150 are initially placed in a first cassette 110. The cassette 110 is a plurality of pockets 112. A tablet 150 is placed in each of the pockets 112 at cassette 110.

Cassette 120 is shown without any tablets. The cassette may be made of metal or other suitable conductor in order to control the potential on the tablets. The cassette may also be made of insulating material. If it is, then the floors of the pockets are coated with an insulator so that the potential on the tablet can be controlled. Note that each pocket 112 has a vacuum aperture 114. Cassette 110 has similar vacuum apertures which are obscured by the tablets 150. FIGS. 17B-17E show one method for applying medicine to both sides of a tablet. The cassette 110 is filled with the tablets 150. A vacuum is applied to the port 116 for holding the tablets 150 in place. Then the cassette 110 is brought proximate to either a single transfer station or an array of transfer stations 130. There the powdered medicine or other coating is transferred to the tablets 150 to provide coatings 135. The coating is fused to the exposed tablet by a suitable fuser. For purposes of explaining the double side coating operation, the fusing operations are omitted. Those skilled in the art understand that fusing occurs after transfer and before the tablets are moved to the other cassette.

Next, as shown in FIG. 17C, a second cassette 120 is arranged over cassette 110 and brought into contact with it so that the pockets 112 of both cassettes are registered. The vacuum on port 116 is released while a vacuum on port 118 is applied. This pulls the tablets 150 up to an engagement with the bottoms of the pockets 112 of the cassette 120. Then the cassette 110 is removed and the cassette 120 is placed proximate the transfer station so that either the same or a different medicine or powder 140 is transferred to the tablets 150 to provide a coating 145 as shown in FIG. 17E.

It is also possible to use two cassettes in a horizontal arrangement with space to part transfer stations. Such an arrangement is shown in FIG. 17F-17H. There the cassette 110 loaded with the tablets 150 is brought proximate on array of transfer heads 160. The transferred material 135 is fixed to the surface of the tablets 150 by a fuser as described above. Next, the cassette 110 is registered with the cassette 120 and the tablets are laterally transferred to cassette 120 by releasing the vacuum on port 116 and applying one to port 118 of cassette 120. Then cassette 120 is moved in front of another array of transfer heads 162 where a second medicine or powder 140 is transferred to the tablets as shown by coating 145.

Figure 18:
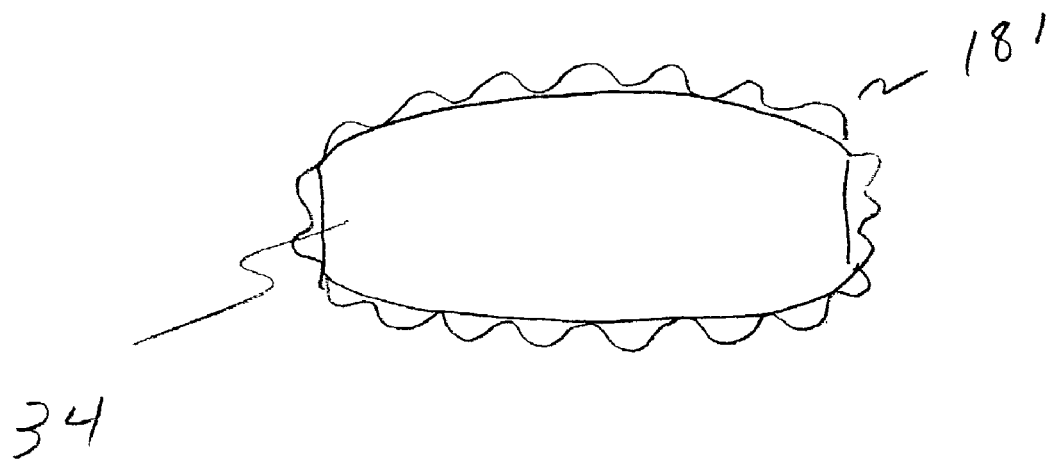
FIG. 18 shows a tablet with a schematic representation of the density of applied powder.

As a consequence of undergoing the method described above, a new tablet is created. The tablet has a surface coating density that varies in accordance with the pitch of the microchannels. See FIG. 18. There a tablet 34 is shown with a variable density of powder. The variable density is represented by wavy line 181. The peaks and valleys of the line correspond to the floors and the tops of the microchannels. The variation is relatively small because the fusing operation tends to equalize the surface distribution of the powder. Nevertheless, one can still detect variations in density. Indeed, with the invention one could even deposit powder in a series of stripes.

CONCLUSION, RAMIFICATIONS, AND SCOPE OF INVENTION

The present invention has the advantages over the prior art of direct deposition of one or more pharmaceutical material in any specific area of a substrate, lower cost, simplicity and small size. From the above descriptions, figures and narratives, the invention's advantages in deposition of pharmaceutical material should be clear.

Although the description, operation and illustrative material above contain many specificities, these specificities should not be construed as limiting the scope of the invention but as merely providing illustrations and examples of some of the preferred embodiments of this invention.

Thus the scope of the invention should be determined by the appended claims and their legal equivalents, rather than by the examples given above.

We claim:

1. An apparatus for coating substrates for a pill, tablet or capsule with a powder comprising:
   an array of a plurality of magnetic brushes disposed on a common axis and each having a rotational magnetic core and a stationary outer shell;
   a magnetic powder supply for supplying a magnetic developer powder to the magnetic brushes
   a print head on the outer shell, the print head defining an array of microchannels for forming a plurality of parallel lines of magnetic developer powder in the microchannels,
   a transfer station spaced from the array of microchannels for transferring simultaneously powder from the print head to a plurality of the substrates for a pill, tablet or capsule;
   control circuitry for operating the print head to transfer simultaneously magnetic development powder to a plurality of the substrates for a pill, tablet or capsule;
   a fuser for fixing the transferred magnetic development powder to a plurality of the substrates for a pill, tablet or capsule; and
   a conveyor carrying simultaneously past the print head and past the transfer station a plurality of substrates for a pill, tablet or capsule where the substrates for a pill, tablet or capsule simultaneously receive deposits of magnetic developer powder and carrying a plurality of the substrates for a pill, tablet or capsule with deposited magnetic developer powder past the fuser where the magnetic develop powder is simultaneously fixed to a plurality of the substrates for a pill, tablet or capsule.

2. The apparatus of claim 1 further comprising two or more arrays of magnetic brushes, each array on a separate, common axis, for transferring magnetic development powder to the three dimensional substrates.

3. The apparatus of claim 2 wherein the powder transferred by the two or more brushes is the same or different from each other.

4. The apparatus of claim 1 further comprising a charged electrode for holding the three dimensional substrates during transfer of powder to the surface of the three dimensional substrates.

5. The apparatus of claim 4 wherein the charged electrode comprises a surface with a vacuum port for applying a vacuum to a surface of the three dimensional substrates opposite the microchannels.

6. The apparatus of claim 1 wherein the print head comprises a substrate having a plurality of elongated, parallel walls separated from each other to define microchannels and each microchannel having one or more transfer electrodes.

7. The apparatus of claim 1 wherein the walls converge at one end of the print head to provide threshold openings for receiving powder that are wider than the microchannel.

8. The apparatus of claim 1 wherein the fuser is a heat lamp.

9. The apparatus of claim 1 further comprising a cassette having a plurality of pockets arranged in rows and columns for receiving and holding the three dimensional substrates, said pockets having one or more vacuum connections for applying a vacuum to the cassette to hold the three dimensional substrates in place.

10. The apparatus of claim 9 further comprising at least two cassettes registerable with each other for transferring three dimensional substrates from one cassette to the other cassette and at least two transfer stations, each associated with one of the cassettes, for transferring powder to opposite exposed surfaces of three dimensional substrates in the cassettes.

11. The apparatus of claim 1 wherein the microchannels are separated from each other by walls and the contour of tops of the walls corresponds to the contour of the three dimensional substrates.

12. The apparatus of claim 1 wherein the three dimensional substrate are conductive.

13. The apparatus of claim 1 wherein the three dimensional substrates are rigid.

14. The apparatus of claim 1 wherein the three dimensional substrates have one or more curved surfaces.

15. The apparatus of claim 1 wherein the three dimensional substrates have an upper surface, a lower surface, and an edge surface between the upper and lower surface sufficient for receiving and holding deposited material.

16. An electrostatic powder deposition apparatus for depositing pharmaceutical powder on defined regions of three dimensional substrates for a pill, tablet or capsule, comprising:
   a) a magnetic brush having a rotating magnetic core and a stationary outer shell;
   b) a developer supply for supplying a magnetic developer powder to the magnetic brushes;
   c) multiple print heads on the outer shell, each print head including:
      an array of microchannels in a substrate for forming a plurality of parallel lines of developer in the channels for simultaneously carrying developer to a plurality of three dimensional substrates for a pill, tablet or capsule,
      a corresponding plurality of transfer electrodes located in the microchannels for selectively transferring developer from the microchannels to a plurality of three dimensional substrates for a pill, tablet or capsule,
      driver circuitry for generating and applying transfer signals to the transfer electrodes,
      a power supply connection for applying power to the driver circuitry,
      a print head input connection for applying print signals to the print head,
      the print signal input including a number of electrical conductors fewer than the number of transfer electrodes,
      logic and control means located on the opposite side of the substrate from the microchannels for applying the print signals to the drive circuitry, and electrical connections between the driver circuitry and the transfer electrodes being formed by via plugs from the bottoms of the microchannels to the opposite side of the substrate;
d) a receiver electrode arranged in spaced relation to the array of microchannels to define a powder transfer region through which a plurality of three dimensional substrates travel simultaneously;
e) a conveyor for carrying simultaneously past the print heads and receiver electrode a plurality of three dimensional substrates where the plurality of the substrates simultaneously receive developer powder.

17. The apparatus of claim 16 wherein the print heads have surfaces curved to compliment curved surface of substrates.

18. The apparatus of claim 17 wherein the print heads have a plurality of concave surfaces for depositing material on a major convex surfaces of substrates and on edges of the substrates or a plurality of complimentary convex regions for depositing material on major concave surfaces of substrates and on edges of substrates.

19. The apparatus of claim 16 wherein the amount of material deposited on the substrates is proportional to the voltage applied to the transfer electrode.

20. The apparatus of claim 16 wherein the deposited material comprise pharmaceutical or time release coatings.

21. The apparatus of claim 16 wherein the deposited material forms a visible image.

22. The apparatus of claim 21 wherein the visible image comprises indicia identifying the deposited pharmaceutical material or the dosage.

23. An apparatus for coating substrates for a pill, tablet or capsule with a powder comprising:
a magnetic brush having a rotational magnetic core and a stationary outer shell;
a magnetic powder supply for supplying a magnetic developer powder to the magnetic brush;
a print head on the outer shell, the print head defining an array of microchannels for forming a plurality of parallel lines of magnetic developer powder in the microchannels,
a transfer station spaced from the array of microchannels for transferring simultaneously powder from the print head to a plurality of the substrates for a pill, tablet or capsule;
control circuitry for operating the print head to transfer simultaneously magnetic development powder to a plurality of the substrates for a pill, tablet or capsule;
a fuser for fixing the transferred magnetic development powder to a plurality of the substrates for a pill, tablet or capsule; and
a carriage having a plurality of pockets for holding the substrates and for carrying the substrates past the print head, transfer station and fuser.

24. The apparatus of claim 23 wherein the carriage comprises a cassette having a plurality of pockets arranged in rows and columns for receiving and holding the three dimensional substrates, said pockets having one or more vacuum connections for applying a vacuum to the cassette to hold the three dimensional substrates in place.

25. The apparatus of claim 24 further comprising at least two cassettes registerable with each other for transferring three dimensional substrates from one cassette to the other cassette and at least two transfer stations, each associated with one of the cassettes, for transferring powder to opposite exposed surfaces of three dimensional substrates in the cassettes.

26. An apparatus for coating substrates for a pill, tablet or capsule with a powder comprising:
a magnetic brush having a rotational magnetic core and a stationary outer shell;
a magnetic powder supply for supplying a magnetic developer powder to the magnetic brush;
a print head on the outer shell, the print head defining an array of microchannels for forming a plurality of parallel lines of magnetic developer powder in the microchannels,
a transfer station spaced from the array of microchannels for transferring simultaneously powder from the print head to a plurality of the substrates for a pill, tablet or capsule;
control circuitry for operating the print head to transfer simultaneously magnetic development powder to a plurality of the substrates for a pill, tablet or capsule;
a fuser for fixing the transferred magnetic development powder to a plurality of the substrates for a pill, tablet or capsule; and
a conveyor having a plurality of pockets, each pocket for holding a substrate including a pill, tablet or capsule for carrying simultaneously past the print head said substrates where the substrates receive deposits of magnetic developer powder and for carrying the substrates with deposited magnetic developer powder past the fuser where the magnetic develop powder is fixed to the substrates.

27. The apparatus of claim 26 wherein said pockets have one or more vacuum connections for applying a vacuum to the cassette to hold the three dimensional substrates in place.

28. The apparatus of claim 26 further comprising at least two cassettes registerable with each other for transferring three dimensional substrates from one cassette to the other cassette and at least two transfer stations, each associated with one of the cassettes, for transferring powder to opposite exposed surfaces of three dimensional substrates in the cassettes.

29. The apparatus of claim 26 wherein the microchannels are longer than they are wide.

30. The apparatus of claim 26 wherein the microchannels are deeper than they are wide.

31. The apparatus of claim 26 wherein the microchannels have a shaped surface corresponding to the shape of the surface of the tablet that receives the transferred powder.

32. The apparatus of claim 26 wherein the magnetic brush comprises an array of a plurality of magnetic brushes disposed on a common axis.

33. The apparatus of claim 32 further comprising two or more arrays of magnetic brushes, each array on a separate, common axis, for transferring power to a tablet.

34. The apparatus of claim 33 wherein the powder transferred by the two or more brushes is the same or different from each other.

35. The apparatus of claim 26 further comprising a charged electrode for holding the tablet during transfer of powder to the surface of the tablet.

36. The apparatus of claim 35 wherein the charged electrode comprises a surface with vacuum port for applying a vacuum to a surface of the tablet opposite the microchannels.

37. The apparatus of claim 26 wherein the printhead comprises a substrate having a plurality of elongated, parallel walls separated from each other to define microchannels and each microchannel having one or more transfer electrodes.

38. The apparatus of claim 26 wherein the walls converge at one end of the printhead to provide threshold openings for receiving powder that are wider than the microchannel.

39. The apparatus of claim 26 wherein the fuser is a heat lamp.

* * * * *